(12) United States Patent
Schulz et al.

(10) Patent No.: US 7,824,184 B2
(45) Date of Patent: Nov. 2, 2010

(54) INTEGRATED CENTRAL MANIFOLD FOR ORTHOPEDIC SIMULATOR

(75) Inventors: Bradley D. Schulz, Savage, MN (US); Paul J. Leska, Sr., Chanhassen, MN (US); Dennis J. Willis, Bloomington, MN (US); Harold F. Fahrendorff, Golden Valley, MN (US)

(73) Assignee: MTS Systems Corporation, Eden Prairie, MN (US)

( * ) Notice: Subject to any disclaimer, the term of this patent is extended or adjusted under 35 U.S.C. 154(b) by 848 days.

(21) Appl. No.: 11/649,961

(22) Filed: Jan. 5, 2007

(65) Prior Publication Data

US 2007/0169566 A1    Jul. 26, 2007

Related U.S. Application Data

(63) Continuation-in-part of application No. 11/332,407, filed on Jan. 13, 2006, and a continuation-in-part of application No. 11/335,974, filed on Jan. 20, 2006.

(60) Provisional application No. 60/760,595, filed on Jan. 20, 2006.

(51) Int. Cl.
    *G09B 23/28* (2006.01)
(52) U.S. Cl. .................................................... 434/262
(58) Field of Classification Search ............... 434/262, 434/267, 268, 270, 272, 274; 73/37
    See application file for complete search history.

(56) References Cited

U.S. PATENT DOCUMENTS

| 3,597,967 A | 8/1971 | Drexler et al. ............ 73/91 |
| 3,658,143 A | 4/1972 | Schwartz ............... 177/208 |
| 3,937,071 A | 2/1976 | Slota et al. ............. 73/809 |
| 4,196,635 A | 4/1980 | Zuber et al. ............. 73/794 |
| 4,318,301 A | 3/1982 | Justice et al. ............ 73/856 |
| 4,428,238 A | 1/1984 | Tauscher ............... 73/663 |
| 4,676,110 A | 6/1987 | Hodo et al. ............. 73/809 |
| 4,882,677 A | 11/1989 | Curran ............... 364/413.02 |
| 5,009,523 A | 4/1991 | Folger et al. ............. 384/475 |
| 5,014,719 A | 5/1991 | McLeod ............... 128/774 |
| 5,151,859 A | 9/1992 | Yoshino et al. ........... 701/23 |
| 5,259,249 A | 11/1993 | Fetto ................... 73/794 |

(Continued)

FOREIGN PATENT DOCUMENTS

DE    27 28 007    6/1977

(Continued)

OTHER PUBLICATIONS

International Search Report/Written Opinion PCT/US07/000797 mailed Feb. 26, 2008.

(Continued)

*Primary Examiner*—Kurt Fernstrom
(74) *Attorney, Agent, or Firm*—Westman, Champlin & Kelly, P.A.

(57) ABSTRACT

An orthopedic simulator is provided with an integral central manifold that provides internal routing of pressurized hydraulic fluid, compressed air, or electrical power to the actuators of the orthopedic simulator. The integral manifold is structurally coupled to support elements and resist and transfer bending and shear forces to the support elements.

20 Claims, 30 Drawing Sheets

U.S. PATENT DOCUMENTS

| | | | |
|---|---|---|---|
| 5,324,247 A | 6/1994 | Lepley | 482/134 |
| 5,327,038 A | 7/1994 | Culp | 310/306 |
| 5,337,758 A | 8/1994 | Moore et al. | 600/594 |
| 5,360,016 A | 11/1994 | Kovacevic | 600/595 |
| 5,403,252 A | 4/1995 | Leon et al. | 482/5 |
| 5,415,661 A | 5/1995 | Holmes | 606/69 |
| 5,511,431 A | 4/1996 | Hinton | 73/806 |
| 5,569,858 A | 10/1996 | Askea et al. | 73/789 |
| 5,670,708 A * | 9/1997 | Vilendrer | 73/37 |
| 5,869,328 A | 2/1999 | Antoci et al. | 435/287.6 |
| 5,936,858 A | 8/1999 | Arai | 700/30 |
| 5,937,530 A | 8/1999 | Masson | 33/534 |
| 5,952,582 A | 9/1999 | Akita | 73/855 |
| 5,959,215 A | 9/1999 | Ono et al. | 73/798 |
| 5,999,168 A | 12/1999 | Rosenberg et al. | 345/161 |
| 6,058,784 A | 5/2000 | Carroll et al. | 73/856 |
| 6,171,812 B1 | 1/2001 | Smith et al. | 435/40.52 |
| 6,230,574 B1 * | 5/2001 | Rider et al. | 73/865.1 |
| 6,418,392 B1 | 7/2002 | Rust et al. | 702/123 |
| 6,447,448 B1 | 9/2002 | Ishikawa et al. | 600/300 |
| 6,447,518 B1 | 9/2002 | Krause et al. | 606/80 |
| 6,472,202 B1 | 10/2002 | Banes | 435/305.1 |
| 0,170,361 A1 | 11/2002 | Vilendrer et al. | 73/849 |
| 6,502,837 B1 | 1/2003 | Hamilton et al. | 280/5.515 |
| 6,510,740 B1 | 1/2003 | Behm et al. | 73/708 |
| 6,538,215 B2 | 3/2003 | Montagnino et al. | 177/25.16 |
| 6,571,373 B1 | 5/2003 | Devins et al. | 716/5 |
| 6,581,437 B2 | 6/2003 | Chrystall et al. | 73/7 |
| 6,629,466 B2 | 10/2003 | Grote et al. | 73/857 |
| 6,645,251 B2 | 11/2003 | Salehi et al. | 623/20.28 |
| 6,659,200 B1 | 12/2003 | Eppink | 175/61 |
| 6,706,005 B2 | 3/2004 | Roy et al. | 600/594 |
| 6,715,336 B1 | 4/2004 | Xu | 73/7 |
| 6,721,922 B1 | 4/2004 | Walters et al. | 716/1 |
| 6,860,156 B1 | 3/2005 | Cavallaro et al. | 73/819 |
| 6,865,954 B2 | 3/2005 | Zubok et al. | 73/804 |
| 7,029,475 B2 | 4/2006 | Panjabi | 606/279 |
| 7,040,177 B2 | 5/2006 | Zubok et al. | 73/804 |
| 7,131,338 B2 | 11/2006 | Zubok et al. | 73/804 |
| 7,204,160 B1 | 4/2007 | Sadegh et al. | 73/862.041 |
| 7,219,555 B2 | 5/2007 | Salvesen | 73/788 |
| 7,284,446 B2 | 10/2007 | Zubok et al. | 73/804 |
| 7,333,111 B2 | 2/2008 | Ng-Thow-Hing et al. | 345/473 |
| 7,357,038 B2 | 4/2008 | Zubok et al. | 73/804 |
| 7,383,738 B2 | 6/2008 | Schulz | 73/781 |
| 7,403,883 B2 * | 7/2008 | Heruth et al. | 703/11 |
| 7,427,199 B2 * | 9/2008 | Sakezles | 434/267 |
| 7,617,744 B2 | 11/2009 | Schulz et al. | 73/865.9 |
| 7,632,100 B2 * | 12/2009 | Allen et al. | 434/273 |
| 7,654,150 B2 | 2/2010 | Schulz et al. | 73/856 |
| 2001/0045941 A1 | 11/2001 | Rosenberg et al. | 345/161 |
| 2002/0029610 A1 | 3/2002 | Chrystall et al. | 73/7 |
| 2002/0166387 A1 | 11/2002 | Grote et al. | 73/857 |
| 2003/0029247 A1 | 2/2003 | Biedermann et al. | 73/768 |
| 2003/0053901 A1 | 3/2003 | Roy et al. | 414/735 |
| 2003/0110830 A1 * | 6/2003 | Dehdashtian et al. | 73/37 |
| 2004/0019382 A1 | 1/2004 | Amirouche et al. | 623/18.11 |
| 2004/0019384 A1 | 1/2004 | Kirking et al. | 623/20.14 |
| 2005/0056099 A1 | 3/2005 | Zubok et al. | 73/804 |
| 2005/0241404 A1 | 11/2005 | Salvesen | 73/788 |
| 2007/0169561 A1 | 7/2007 | Schulz et al. | 73/794 |
| 2007/0169565 A1 | 7/2007 | Schulz et al. | 73/862.08 |
| 2007/0169567 A1 | 7/2007 | Schulz et al. | 73/862.08 |
| 2007/0169572 A1 | 7/2007 | Schulz et al. | 73/865.3 |
| 2007/0169573 A1 | 7/2007 | Schulz et al. | 73/865.6 |

FOREIGN PATENT DOCUMENTS

| | | |
|---|---|---|
| DE | 44 11 508 A1 | 2/1994 |
| EP | 0 919 201 A1 | 9/1998 |
| GB | 1108652 * | 4/1968 |

OTHER PUBLICATIONS

International Preliminary Report on Patentability PCT/US07/000797 dated Jul. 15, 2008.

Biomechanical Materials Testing Laboratory [online]. Flinders University, Adelaide, Australia, 2003 [retrieved on Aug. 7, 2007]. Retrieved from www.archive.org using the Internet: <URL: http://web.archive.org/web/20030825155452/http://som.flinders.edu.au/FUSA/ORTHOWEB/lab.Htm>. p. 3,para 7,p. 1, para 3,p. 3, para 3, p. 2, para 7, p. 2, para 11; 4 pages.

"Notification of Transmittal of the International Search Report and the Written Opinion of the International Searching Authority, or the Declaration" for related foreign application No. PCT/US/2007/00727 filed Jan. 10, 2007; date of mailing May 8, 2008; 8 pages.

"Notification of Transmittal of the International Search Report and the Written Opinion of the International Searching Authority, or the Declaration" for related foreign application No. PCT/US/2007/00799 filed Jan. 10, 2007; date of mailing Jul. 15, 2008; 8 pages.

"Notification of Transmittal of the International Search Report and the Written Opinion of the International Searching Authority, or the Declaration" for related foreign application No. PCT/US/2007/00796 filed Jan. 10, 2007; date of mailing Mar. 27, 2008; 11 pages.

"Notification of Transmittal of the International Search Report and the Written Opinion of the International Searching Authority, or the Declaration" for related foreign application No. PCT/US/2007/00733 filed Jan. 10, 2007; date of mailing Oct. 1, 2007; 8 pages.

International Preliminary Report on Patentability PCT/US07/00796 dated Jul. 15, 2008; one page.

International Preliminary Report on Patentability PCT/US07/00799 dated Aug. 26, 2008; one page.

International Search Report PCT./US/07/00727 dated Dec. 28, 2004, one page.

International Preliminary Report on Patentability PCT/US07/00727 dated Jul. 15, 2008; one page.

Written Opinion of the International Searching Authority PCT/US07/00727 mailed May 5, 2008; 3 pages.

Prosthetic Knee Tester, 6 Station Knee Simulator [online]. ATMI-Boston, Nov. 6, 2005 [retrieved on Jul. 6, 2007.] Retrieved from the Internet: <URL: http://web.archive.org/web/20051106114417/http://www.amtiweb.com/sim/knee_machine1.htm> Entire document.

PCT International Search Report and Written Opinion of the International Searching Authority, PCT/US2004/040798 dated Jun. 4, 2005; one page.

"Notification of Transmittal of the International Search Report and the Written Opinion of the International Searching Authority, or the Declaration" for related International application No. PCT/US07/00726 filed Jan. 10, 2007, 9 pages.

* cited by examiner

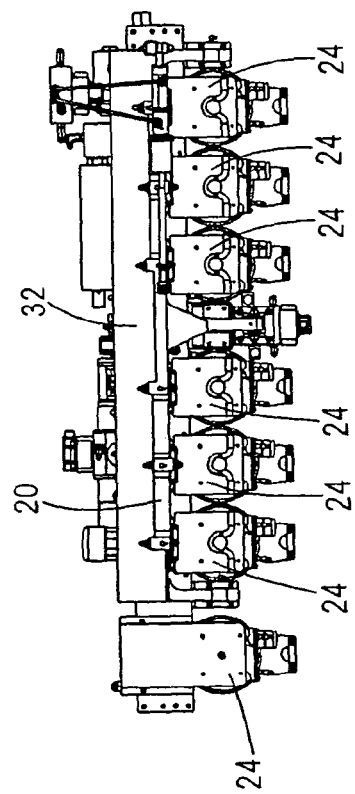
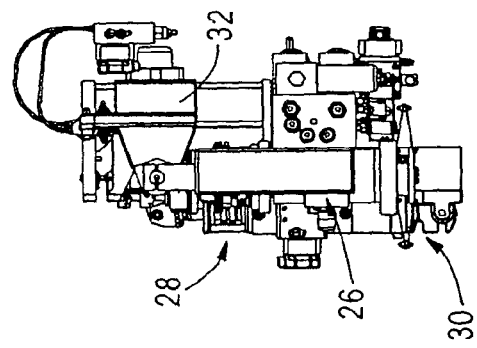
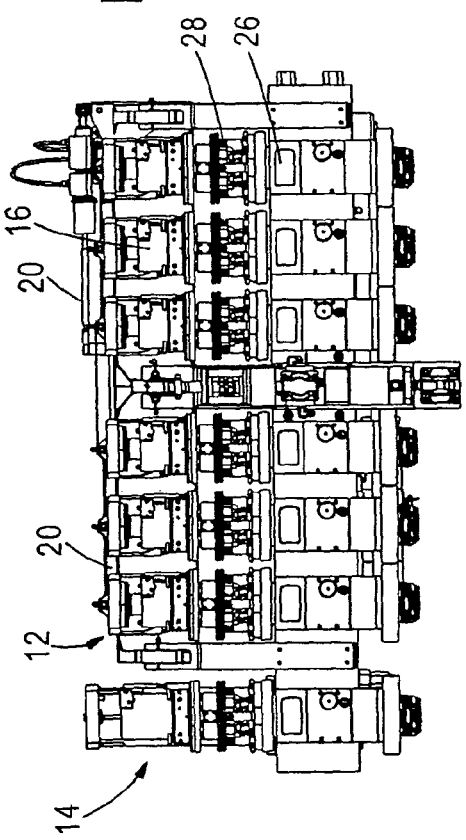
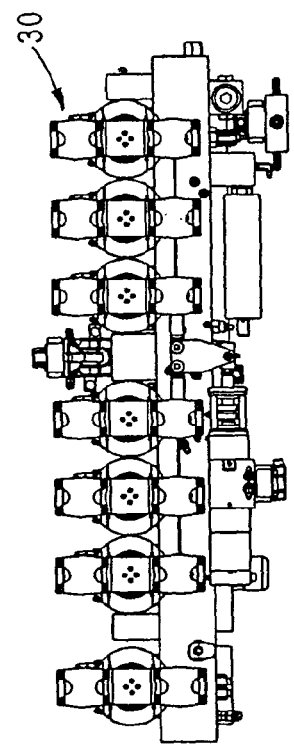

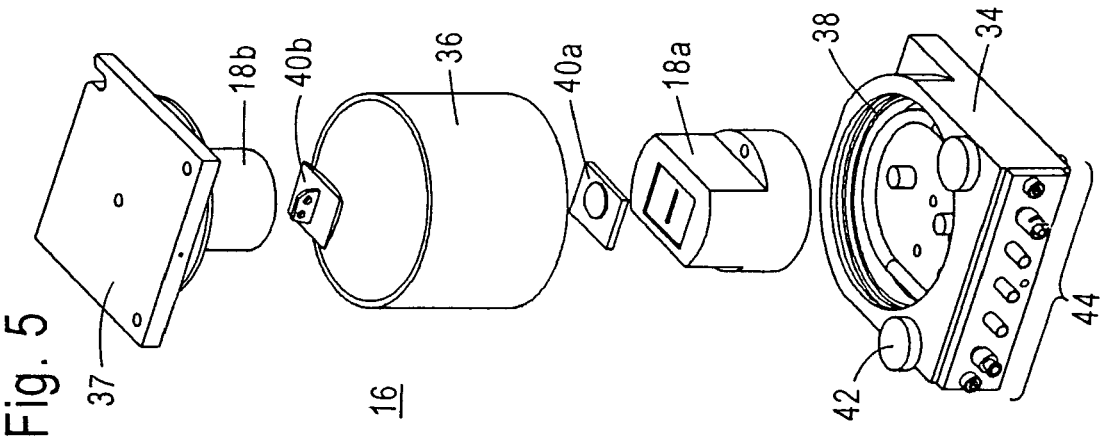
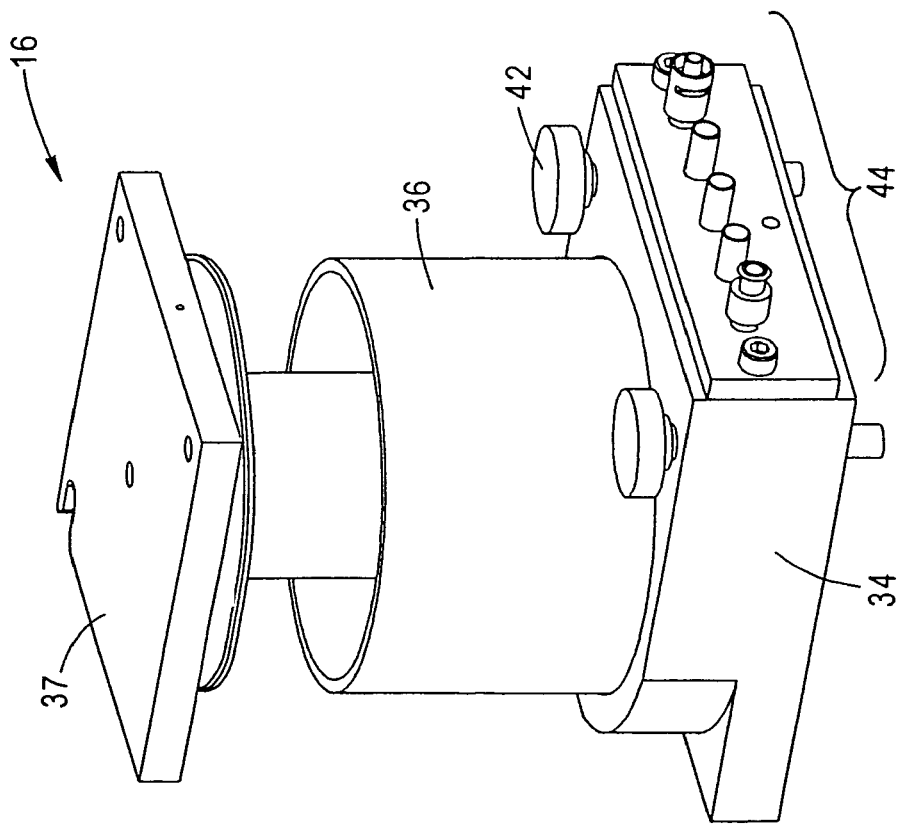

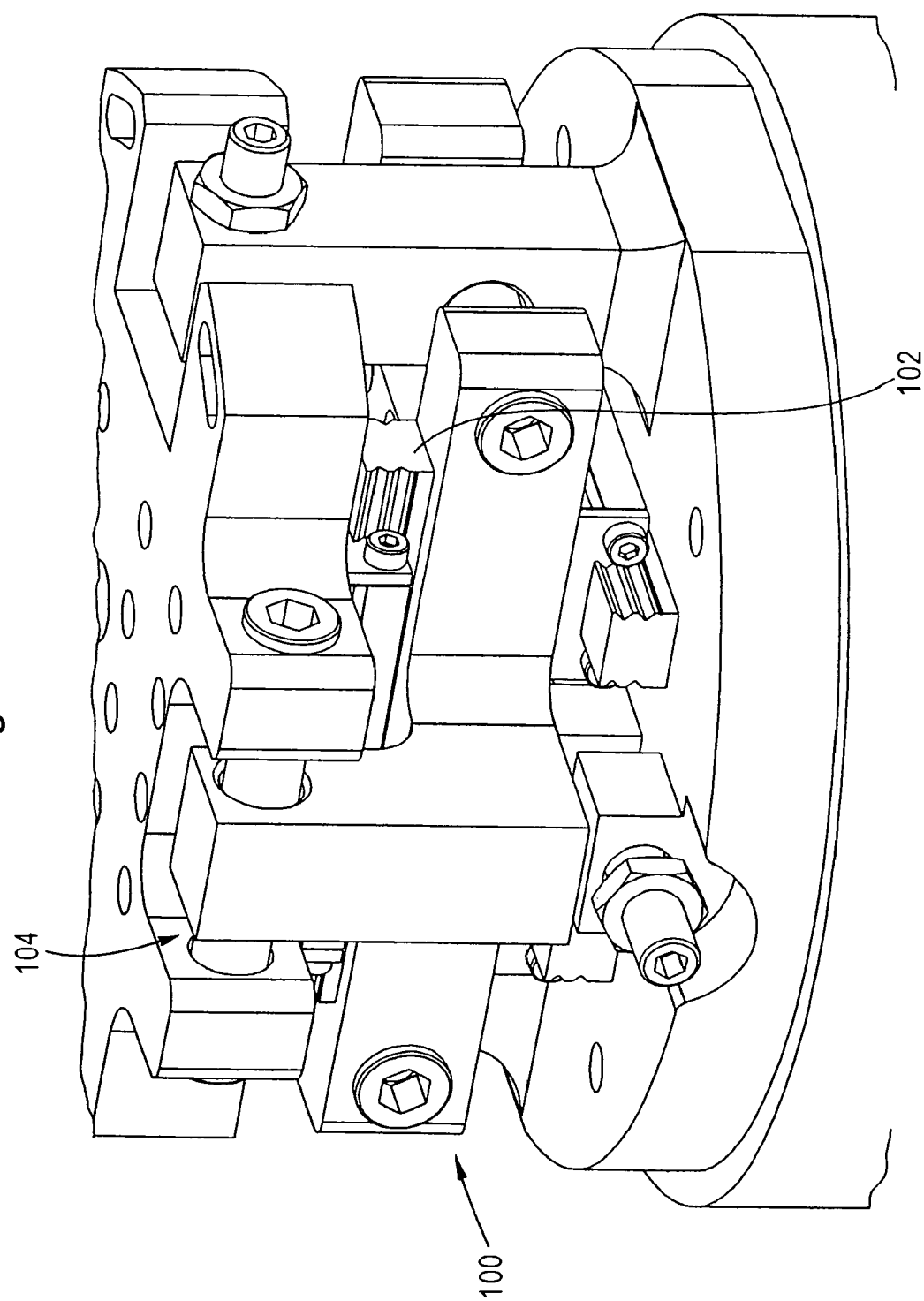

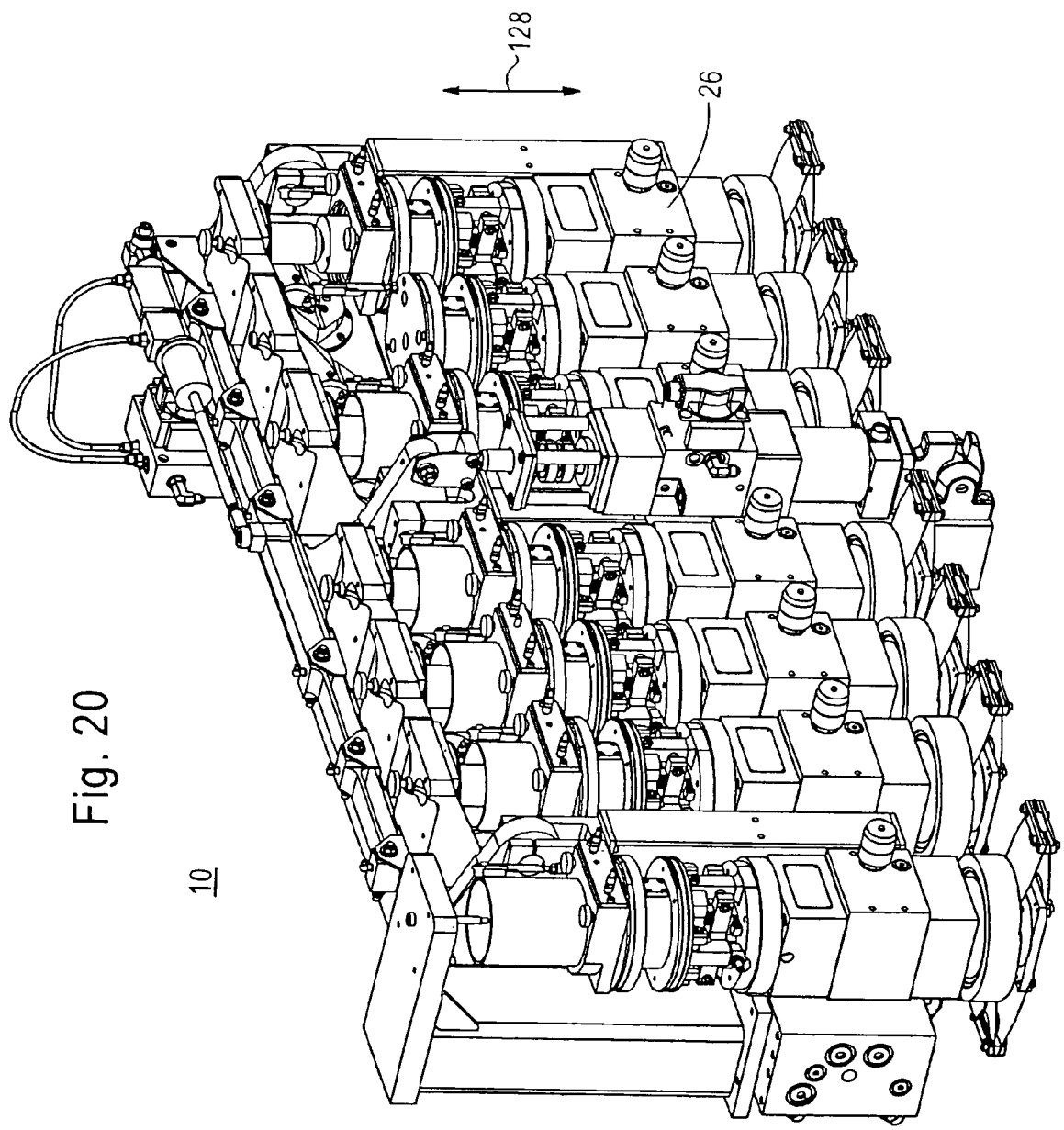

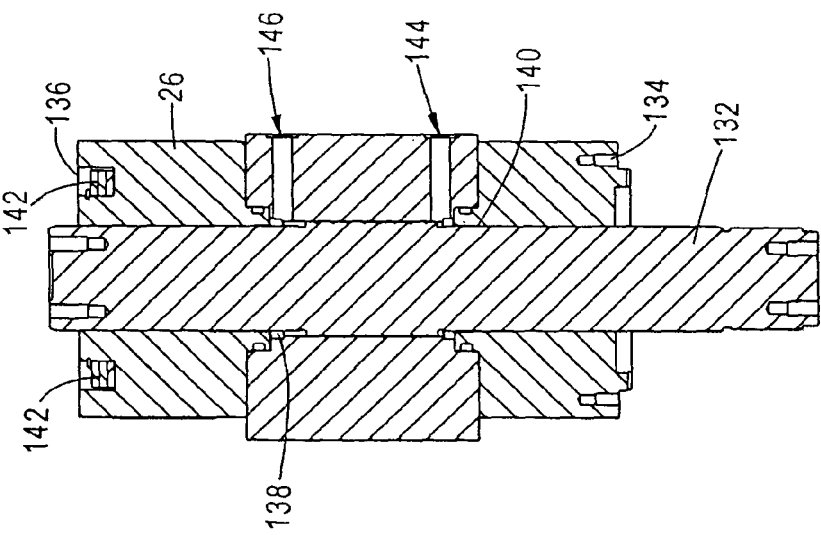
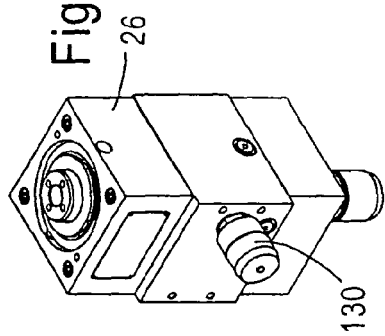
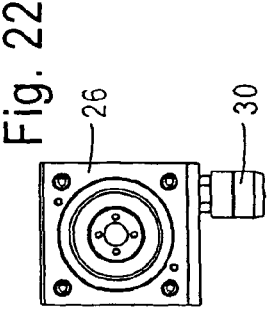
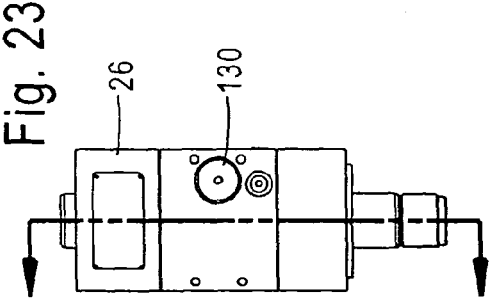

INTEGRATED CENTRAL MANIFOLD FOR
ORTHOPEDIC SIMULATOR

RELATED APPLICATIONS

The present application claims priority to Provisional Patent Application 60/760,595 filed Jan. 20, 2006, U.S. patent application Ser. No. 11/332,407, filed Jan. 13, 2006 and U.S. patent application Ser. No. 11/335,974 filed Jan. 20, 2006 the contents of which are incorporated herein, by reference, in their entirety. This application is a continuation-in-part of U.S. patent application Ser. No. 11/332,407, filed Jan. 13, 2006 and continuation-in-part of U.S. patent application Ser. No. 11/335,974 filed Jan. 20, 2006.

FIELD

The embodiments of the present invention relate to the field of orthopedic simulators, such as spinal implant wear test machines.

BACKGROUND

There is an ever increasing need for testing of orthopedic devices. Such testing may be required for certification of the devices. For example, wear testing of spinal implants are subject to ISO and ASTM standards. In the example of a spinal wear implant, the test procedure defines the relative angular movement between articulating components, and specifies the pattern of the applied force, speed and duration of testing, sample configuration and test environment to be used for the wear testing of total intervertebral spinal disk prostheses. While the test method focuses on wear testing, additional mechanical tests such as fatigue testing and others can be required. Spinal implants are only one type of orthopedic device. Others include, for example, hip-joint prostheses, knee-joints, etc. Such devices also need to be tested.

An orthopedic simulator may require extensive routing of the operating fluid for force actuators that apply testing forces to test specimens. Operating fluid can be a liquid, such as hydraulic fluid, or a gas such as air. The extensive routing can add to the size of the simulator due to the many tubes and connections that are typically required for hydraulic or pneumatic systems. Similar concerns hold true for systems that employ electrical connections and wiring to control the actuators. Further, assembly may be difficult and with multiple connections, there is a relatively high likelihood of leaks. Also, the various mechanical movements of the actuators can cause undesirable vibrations in the simulator during operation.

SUMMARY

There is a need for improving the fluid routing of operating fluid in an orthopedic simulator, and also structurally strengthening the simulator without adding to the size or complexity of the machine.

These and other needs are met by certain embodiments of the present invention which provide an integral central manifold arrangement for an orthopedic simulator comprising a substantially solid block of material forming a manifold housing. A fluid tube is provided within the manifold housing, and fluid inlets and outlets are configured to fluidically couple the fluid tube to the orthopedic simulator.

The earlier stated needs are also met by embodiments of the invention that provide an orthopedic simulator comprising a plurality of test stations, a plurality of actuators coupled to the test stations, and support components that support the test stations. An integral manifold is provided that is structurally coupled to the support components and is fluidically coupled to the plurality of actuators.

By keeping the plumbing internal to the manifold itself, rather than external, the orthopedic simulator may be made more compact than otherwise. Another advantage provided by certain embodiments is the maintaining of the flow paths from a servo control to each individual vertical actuator similar in terms of pressure loss.

An orthopedic simulator comprising a plurality of test stations, a plurality of actuators coupled to the test stations, support elements that support the test stations, and an integral manifold that is structurally coupled to the support elements and contains operating power transmission carriers that are coupled to the plurality of actuators. In certain embodiments, the operating power transmission carriers comprise hydraulic tubing, or pneumatic tubing, or electrical wiring.

The foregoing and other features, aspects and advantages of the disclosed embodiments will become more apparent from the following detailed description and accompanying drawings.

BRIEF DESCRIPTION OF THE DRAWINGS

FIG. 2a is a top view of the orthopedic simulator of FIG. 1; FIG. 2b is a front view; FIG. 2c is a bottom view and FIG. 2d is a side view.

FIG. 4 depicts an exemplary embodiment of an assembled specimen containment module.

FIG. 5 is an exploded view of the specimen containment module of FIG. 4.

FIG. 17 depicts a portion of an x-y slide assembly in accordance with embodiments of the present invention.

FIG. 20 is a perspective view of the orthopedic simulator of FIG. 1, with an indication of loading in a vertical direction.

FIG. 21 is a perspective view of an embodiment of an actuator in isolation.

FIG. 22 is a top view of the actuator of FIG. 21.

FIG. 23 is a side view of the actuator of FIG. 21.

FIG. 24 is a cross-sectional view of the actuator of FIG. 21.

DETAILED DESCRIPTION

Embodiments of the present invention address problems relating to the routing of fluids in an orthopedic simulator, as well as vibrations during machine operation. The embodiments solve these problems, at least in part, by providing an integral central manifold arrangement for an orthopedic simulator. The manifold may be formed of a substantially solid block of material, forming a manifold housing. A plurality of fluid tubes can be provided in the integral central manifold. The fluid tubes provide fluid connectivity in a compact manner, and allows for a greater balancing of fluid and reduced plumbing. The integral central manifold can also serve as a structural element, and resists and transfers bending and shear forces to vertical supports, as well as provide cross-bracing in certain embodiments.

The orthopedic simulator of the present invention may be employed, for example, as a spinal implant wear test machine. In such a configuration, the intent of ISO 18192 is satisfied. The orthopedic simulator is designed for accuracy as well as increased speed.

In the following description, is assumed that the orthopedic simulator is a spinal implant wear test machine, but it should be apparent to those of ordinary skill in the art that this is exemplary only. The features, concepts and designs depicted in the following figures and description may be employed in other types of machines and orthopedic simulators.

Figure 1:
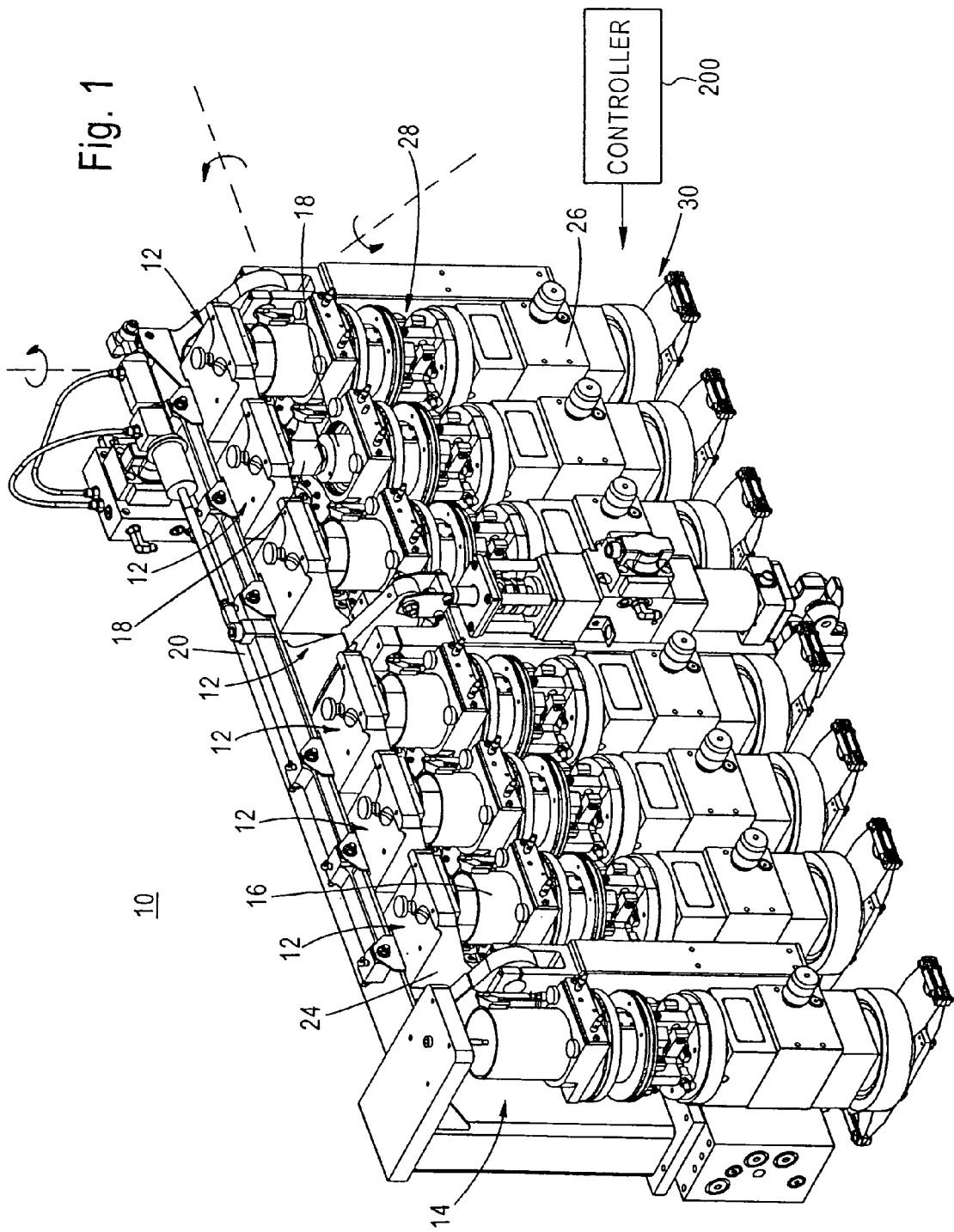
FIG. 1 is a front, perspective view of an orthopedic simulator in accordance with certain embodiments of the invention, with an external housing removed for illustrative purposes, and with forces being schematically depicted.

FIG. 1 depicts an orthopedic simulator 10 for testing of test specimens of orthopedic devices. The orthopedic simulator 10 has a plurality of test stations 12. In the illustrated embodiment, there are six test stations 12 in which specimens are subjected to the forces applied by the machine 10, and a control station 14 that holds a specimen that is not subjected to all of the forces provided at the other test stations 12.

The orthopedic simulator 10 is able to provide forces Fx, Fy, and Fz in the x, y and z directions as depicted in FIG. 1, shown with the x, y and z axes at one of the test stations 12. Additionally, torques may be applied around the x, y and z axes, as depicted. The test specimen is not shown in FIG. 1 so as not to obscure the present invention. In the spinal implant wear testing machine according to certain embodiments of the invention, a specimen containment module is provided that contains fluids in which the test specimen is immersed. Upper and lower adapters 18 (only seen clearly at one of the test stations 12 in which the specimen chamber is removed for illustrative purposes) hold the test specimens between them within the specimen containment module 16.

A linkage 20 provides forces in the x direction with the linkage 22 providing forces in the y direction. Gimbals 24 are connected to the upper adapters 18 and may be moved around the y axis and around the x axis to provide moments around the x and y axes.

Vertical loads, represented by forces along the z axis, are provided by vertical load actuators 26, as shown in FIG. 1. Although different types of actuators may be employed, a friction-free axial actuator is preferable to provide for a friction-free axial/torsion actuation system. The vertical load actuator 26 applies a vertical loading along the z axis through components 28 to the test specimen via the lower adapter 18. In the illustrated embodiment, which will be described in more detail later, the components 28 include an x-y slide table and a load cell.

The vertical load actuators 26, and the actuators driving the linkages 20 and 22 are coupled to a central manifold 92. Operating fluid for the different actuators of the orthopedic simulator is routed through the central manifold 92. As will be described in more detail later, this routing through the central manifold 92 has a number of benefits, including reducing the amount of plumbing, reducing the overall size of the simulator and achieving a greater balancing of fluid within the system. Also, the integral nature of the central manifold 92 and its structure allows the central manifold 92 to resist and transfer bending and shear forces to vertical components of the machine, and be employed in a cross-bracing manner to solidify the simulator.

The embodiments of the invention are described below with examples that relate to an orthopedic simulator in which the actuators are fluidically operated, either hydraulically or pneumatically. Certain other embodiments may be provided in which the actuators are electrically operated, so that the central manifold does not contain fluid plumbing, but rather electrical connections and wiring for the simulator. Hence, when describing the integral nature of the central manifold of the present invention, it is to be understood that the embodiments of the invention apply to hydraulic, pneumatic or electric systems. For purposes of description, however, the embodiments will be referred to in the following with respect to hydraulic and pneumatic systems only.

It is desirable to provide a transmission of drive torque with little deflection related error, having high torsional stiffness. At the same time, low axial stiffness is desirable so that there is little cross-talk onto the vertical loading and so the cross-talk is not seen at the load cell. An axial rotation linkage 30 is coupled to the vertical load actuator 26. The motion of the axial rotation linkage 30 is around the vertical axis z, as depicted in FIG. 1. Although the axial rotation linkage 30 is depicted at the bottom of FIG. 1, it should be apparent to those of skill in the art that the structure depicted in FIG. 1 is suspended vertically so that the axial rotation linkages 30 are free to rotate. This will become more apparent in later-described figures.

FIGS. 2a-2d depict alternate views of the orthopedic simulator 10. FIG. 2a is a top view which best shows the arrangement of the linkages 20 with the gimbals 24. A crosshead 32 is provided, which may also best be seen in FIG. 2d. FIG. 2a is a top view, while FIG. 2b is a front view, FIG. 2c is a bottom view and FIG. 2d is a side view.

Figure 3:
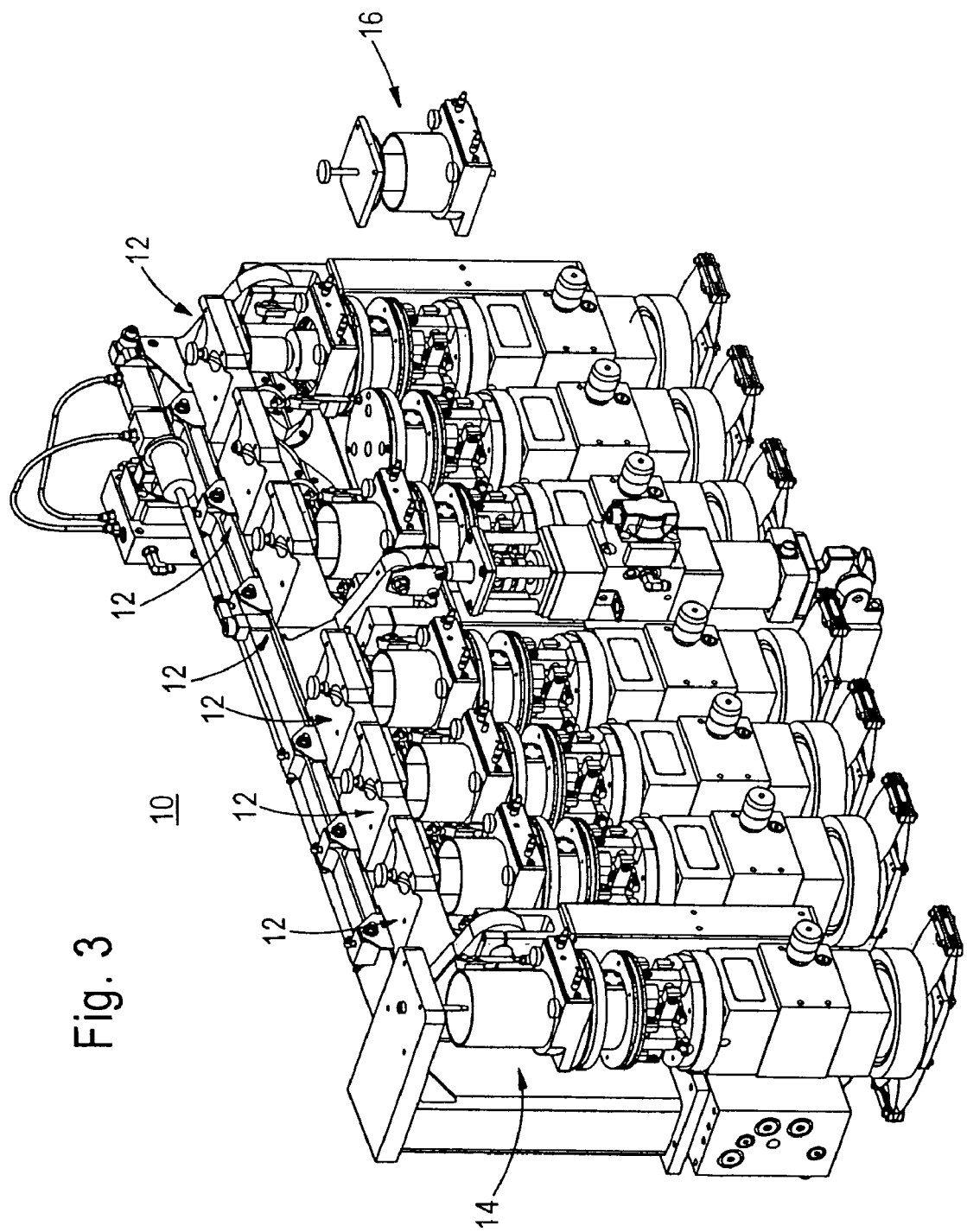
FIG. 3 is a view similar to FIG. 1, illustrating the removability of a specimen containment module.

FIG. 3 depicts a perspective view of the orthopedic simulator of FIG. 1, with a specimen containment module 16 that is remote from the orthopedic simulator 10. The specimen containment modules 16 are releasably attachable to the test station 12. The releasable attachment feature of each of the specimen containment modules 16 enables bench top preparation work on the test specimen to be performed remotely from the environment of the orthopedic simulator 30. This remote loading and preparation capability allows for careful removal and insertion of delicate test specimens. Further, the mounting of one-piece specimens is facilitated with this arrangement. An important consideration is the reduction in the contamination potential created by remotely mounting a specimen within the specimen containment module. The specimen containment module 16 also contains adapters 18 that are designed for flexibility, ease of manufacturing and low cost.

An exemplary embodiment of a specimen containment module 16 is shown in isolation in FIG. 4, and in exploded view in FIG. 5. The specimen containment module contains a base 34 and upper connector 37 that interface to a test station 12 and at which the specimen containment module 16 is releasably attached to the orthopedic simulator 10. A chamber 36, when inserted into the moat 38 in the base 34, forms a fluid container with the base 34. A test specimen 40 is depicted with a lower portion 40a and an upper portion 40b. However, certain test specimens may also be one-piece specimens.

Releasable fasteners 42, such as thumb screws, may be employed to releasably attach the specimen containment module 16 to the orthopedic simulator 10. Fluid connections 44 are used to provide fluid as will be described in more detail in the following figures.

Figure 6:
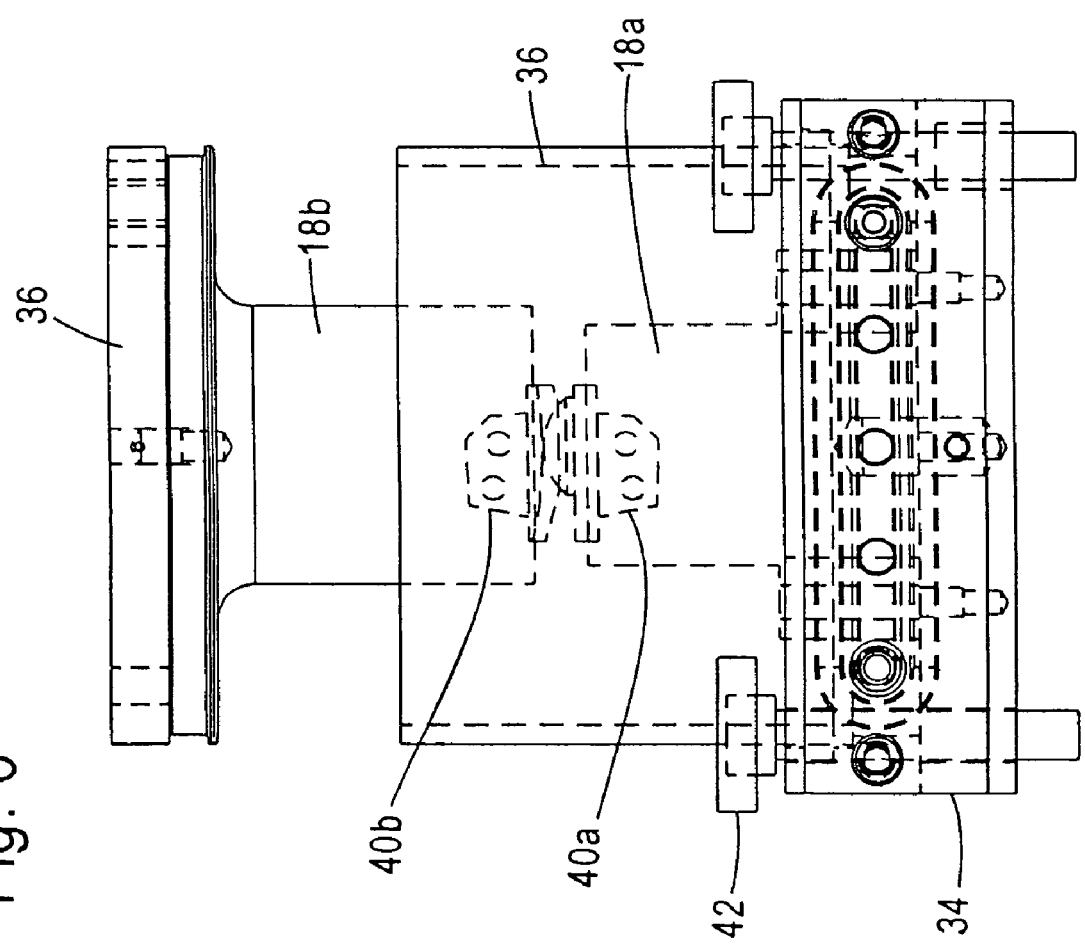
FIG. 6 is a side, partially cross-sectional view of the specimen containment module of FIG. 4.

FIG. 6 is a side, partially cross-sectional view of the specimen containment module 16 of FIGS. 4 and 5. The test specimen 40 is shown with the upper and lower portions coupled together, as seen in FIG. 6.

Figure 7:
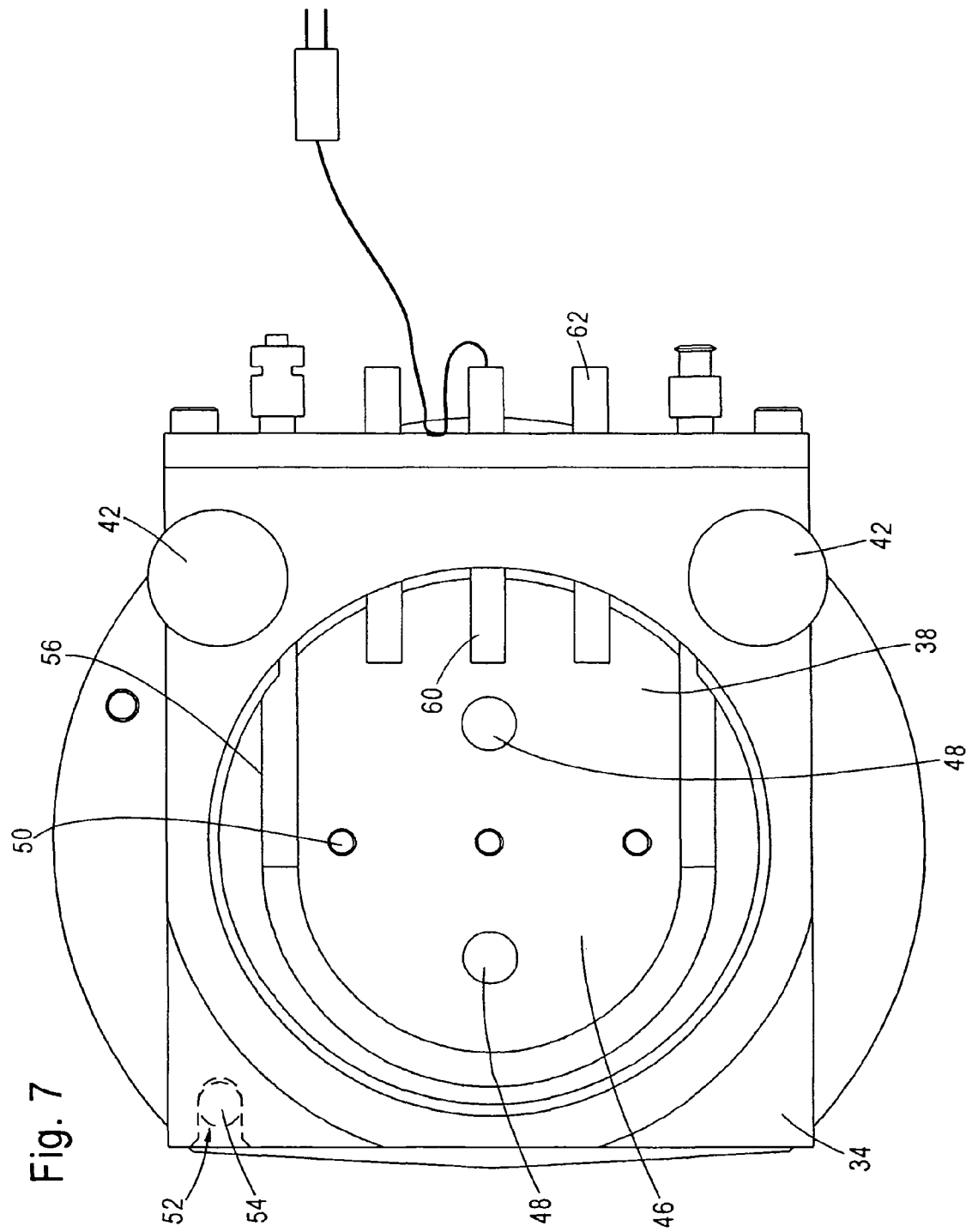
FIG. 7 is a top view of a base of the specimen containment module of FIG. 4.

FIG. 7 is a top view of the base 34. A specimen mounting platform 46 is provided which includes two pins 48, with one pin piloting and another pin interacting with a slot in the lower adapter 18a for anti-rotation purposes. Screw holes 50 are depicted and may be employed to provide a specimen hold down function.

The base 34 also includes a recess 52 that is able to interact with a pin 54 on the orthopedic simulator 10. This provides a slidable installation of the specimen containment module 16. A tubing loop 56 is provided within the base to provide a temperature control of the bath in which the test specimen 40 is immersed. As will be described in more detail, a temperature control fluid is circulated through the tubing loop 56 to precisely control the temperature of the bath.

Recesses 58 provide for thumb screws or other releasable fasteners to secure the specimen containment module 16 to the orthopedic simulator 10. A temperature probe 60 provides feedback on the temperature of the bath and can be used to control the temperature control fluid.

Bath fluid circulation tubes 62 are used to circulate bath fluid within the fluid container formed by the base 34 and the chamber 36.

Figure 8:
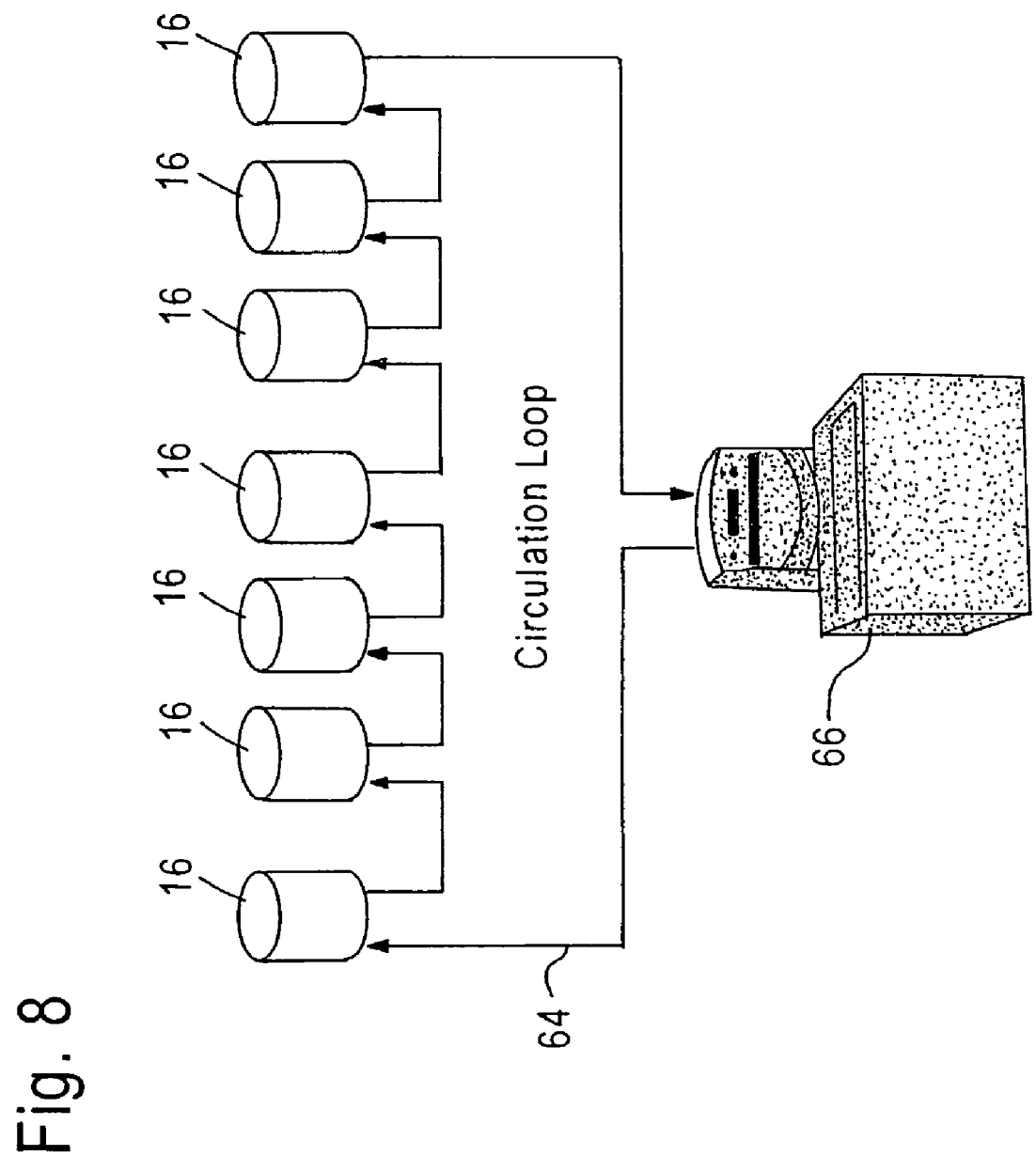
FIG. 8 is a schematic depiction of an embodiment of a circulation loop for circulating a temperature control fluid in a temperature control circuit.

FIG. 8 depicts a circulation loop for circulating the temperature control fluid in the temperature control circuit. The temperature control fluid is circulated in each of the specimen containment modules through the tubing loops 56, as seen in FIG. 7. A single circulation loop 64 circulates a temperature control fluid, such as water, through the closed loop system. The tempered water is circulated through the heat exchangers in each of the baths of the specimen containment modules. The heater 66 provides a precise control and circulation of the tempered water. This daisy-chained approach produces a very stable temperature in each of the baths at the specimen containment modules 16. In certain embodiments, not shown, each of the baths may be individually controlled with separate circulation loops for each bath. However, the embodiment depicted in FIG. 8 is preferred. This arrangement also has the advantage over electric heating elements or other types of heating, in preventing overtemperature related fluid degradation.

Figure 9:
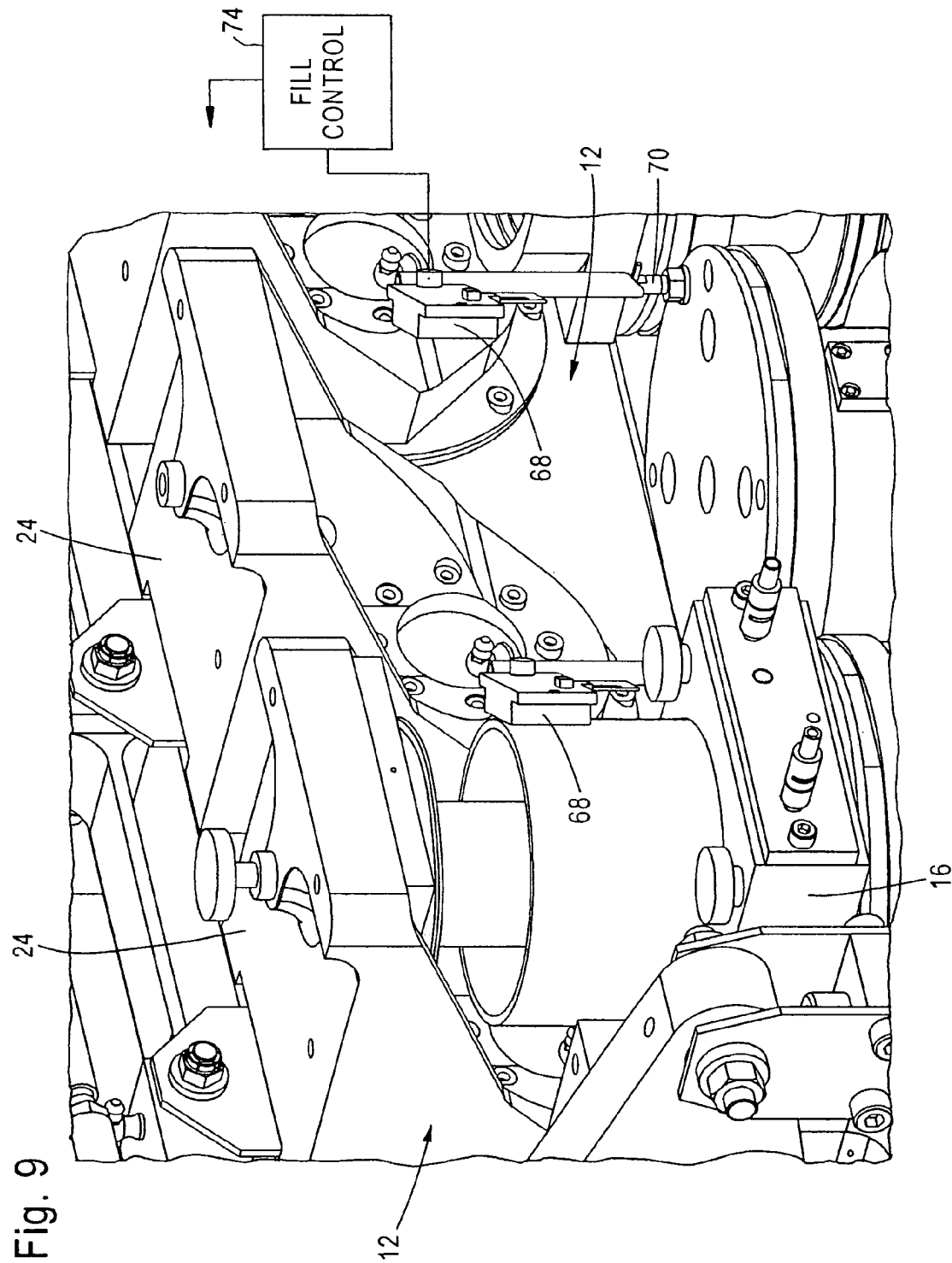
FIG. 9 depicts two test stations, with one test station having a specimen containment module releasably attached thereto.

FIG. 9 depicts two test stations 12, one of which has a specimen containment module 16 releasably attached thereto. A non-contact level sensor 68, such as those known in the sensing art, are provided on posts 70 near the chamber 36. The height of the non-contact level sensor 68 may be adjusted along the pillar 70 in the direction of arrow 72. This allows the desired fluid height within the chamber 36 to be precisely adjusted. The non-contact level sensor 68 provides its signals to a fill controller 74, schematically indicated as being connected to a non-contact level sensor 68. The fill control 74, based upon the signals received from the non-contact level sensors 68, determines whether the fluid in the specimen containment module 16 needs to be replenished. The test fluid, such as bovine fluid, for example, may evaporate to some extent, thereby increasing the concentration of the fluid. Distilled water is furnished (through a fill tube, not shown) under the control of the fill control 74.

Figure 10:
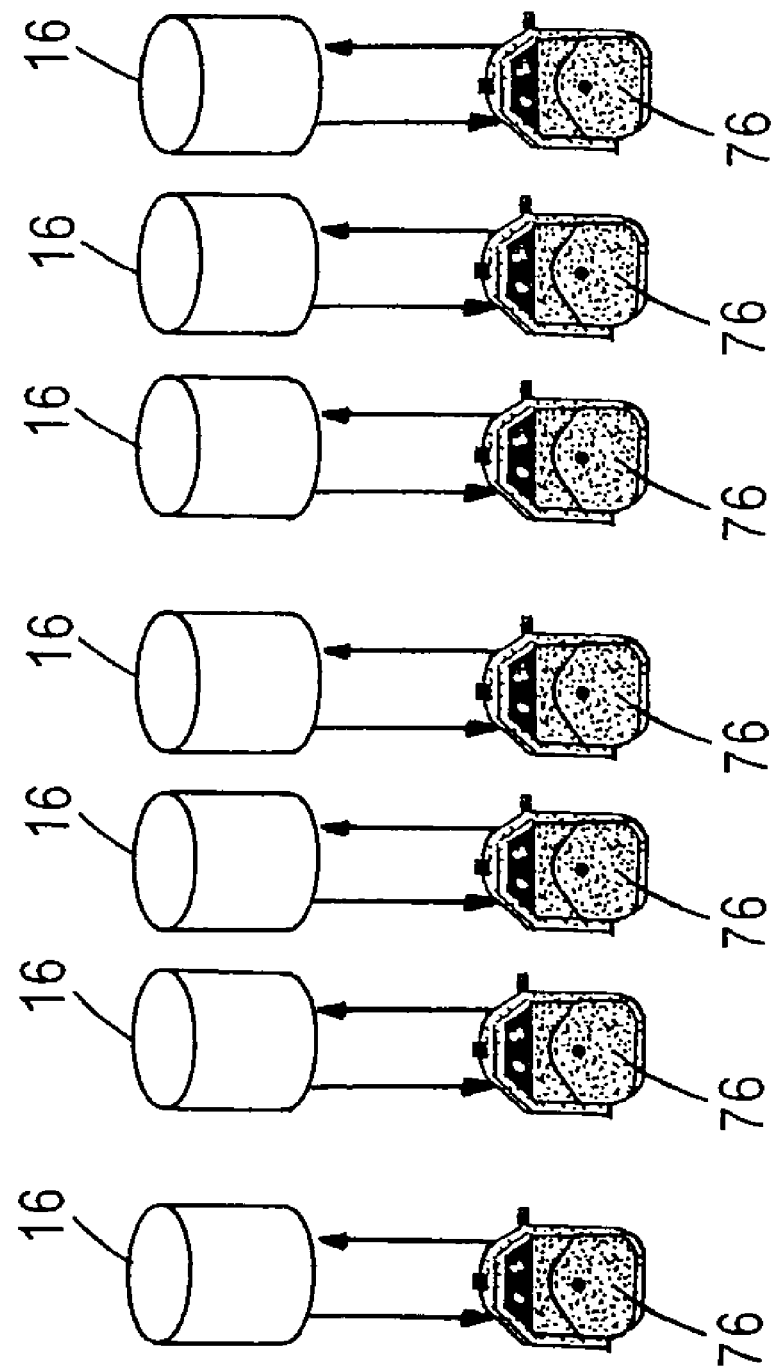
FIG. 10 schematically depicts an exemplary arrangement for circulating bath fluid.

An arrangement for the circulation of the bath fluid is depicted in FIG. 10. Unlike the temperature control fluid, individual loops are preferred in order to maintain each test specimen and bath in its own environment. In other words, cross-contamination of wear particles is avoided by providing the individual loops for each specimen module. In certain embodiments, peristaltic pumps 76 are employed for each of the individual loops. A stirring action is provided.

Figure 11:
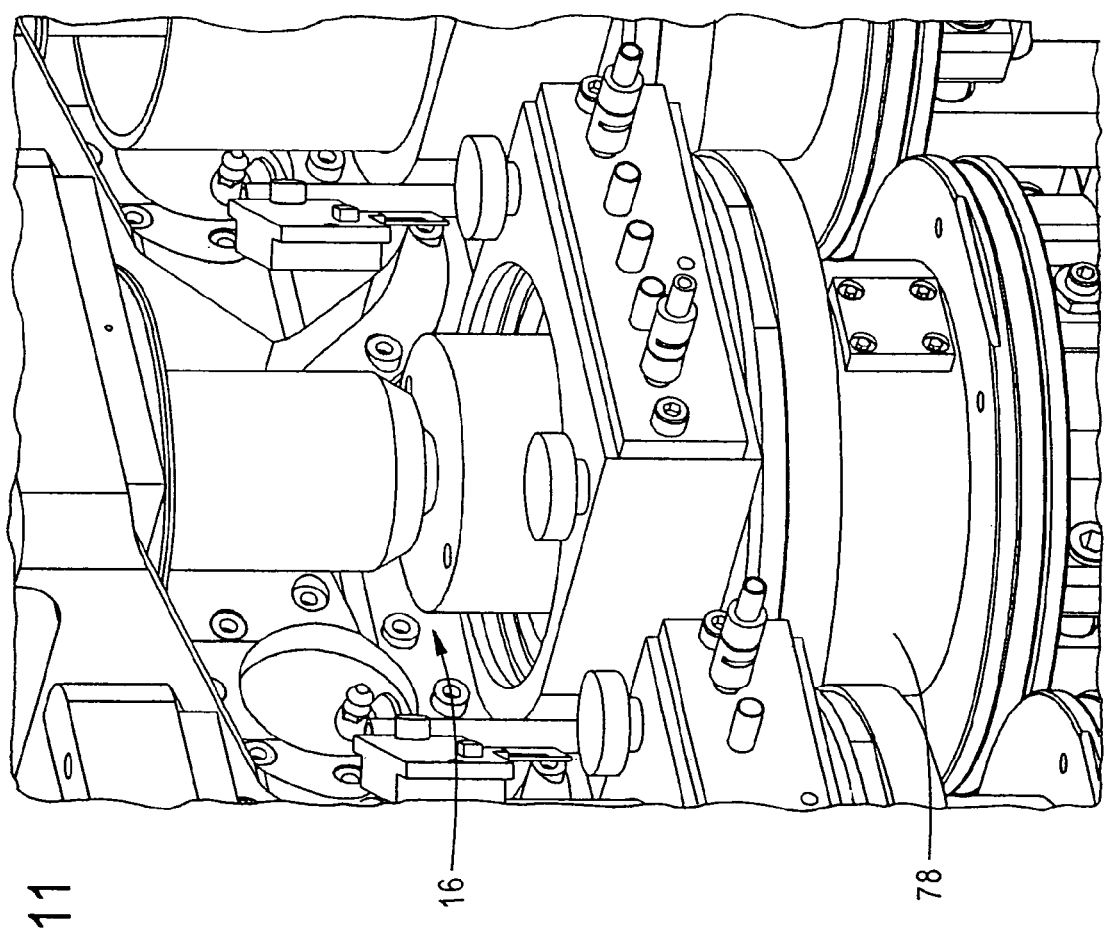
FIG. 11 depicts an embodiment of a specimen containment module in an installed position.

FIG. 11 shows a specimen containment module 16 (without the chamber 36 for illustrative purposes) in an installed position within the orthopedic simulator 10. The specimen containment module is releasably attached at its base 34 to a load cell module 78. The load cell module is designed to accommodate either a single or multi-axis force transducer. In the illustrated embodiment, a single axis transducer is depicted.

Figure 12:
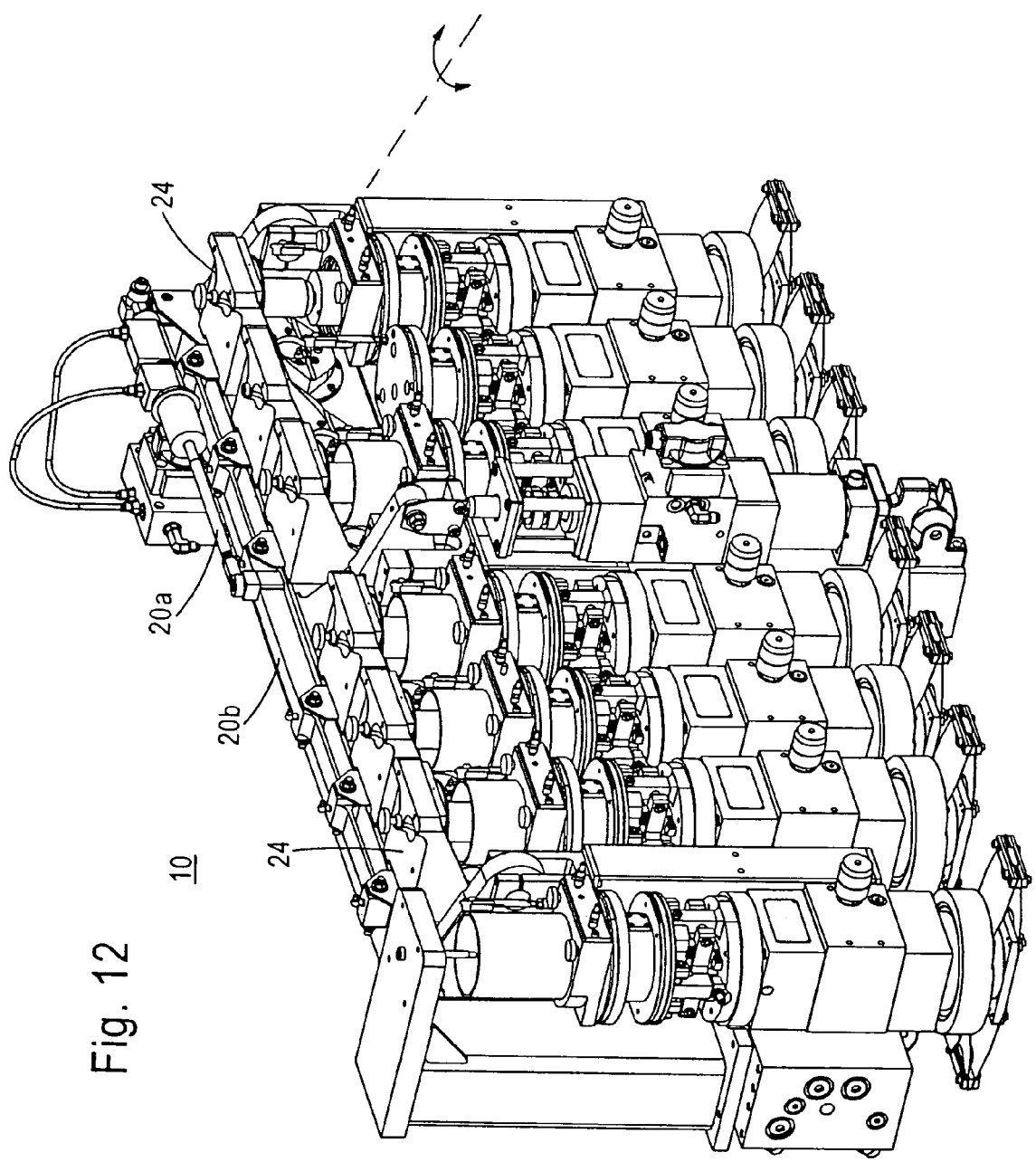
FIG. 12 is a perspective view of the orthopedic simulator of FIG. 1, with an indication of the flexion and extension motion.

FIG. 12 depicts the orthopedic simulator 10 and exemplifies the flexion/extension motion. The linear actuator 20a of the linkage 20 extends back and forth in an axial manner, causing the connecting link 20b to translate in an axial direction. This causes the inner gimbals 24 at the test stations 12 to move and rotate around an axis of rotation depicted in FIG. 12.

Although not shown, the connecting link 20b and connections to the inner gimbals 24 employ high quality bearings, such as long life needle bearings used at key points. The design insures a long life and low lash, creating an accurate machine for a long term use. The low moving mass linkage depicted maximizes performance and is designed for ease of maintenance.

Figure 13:
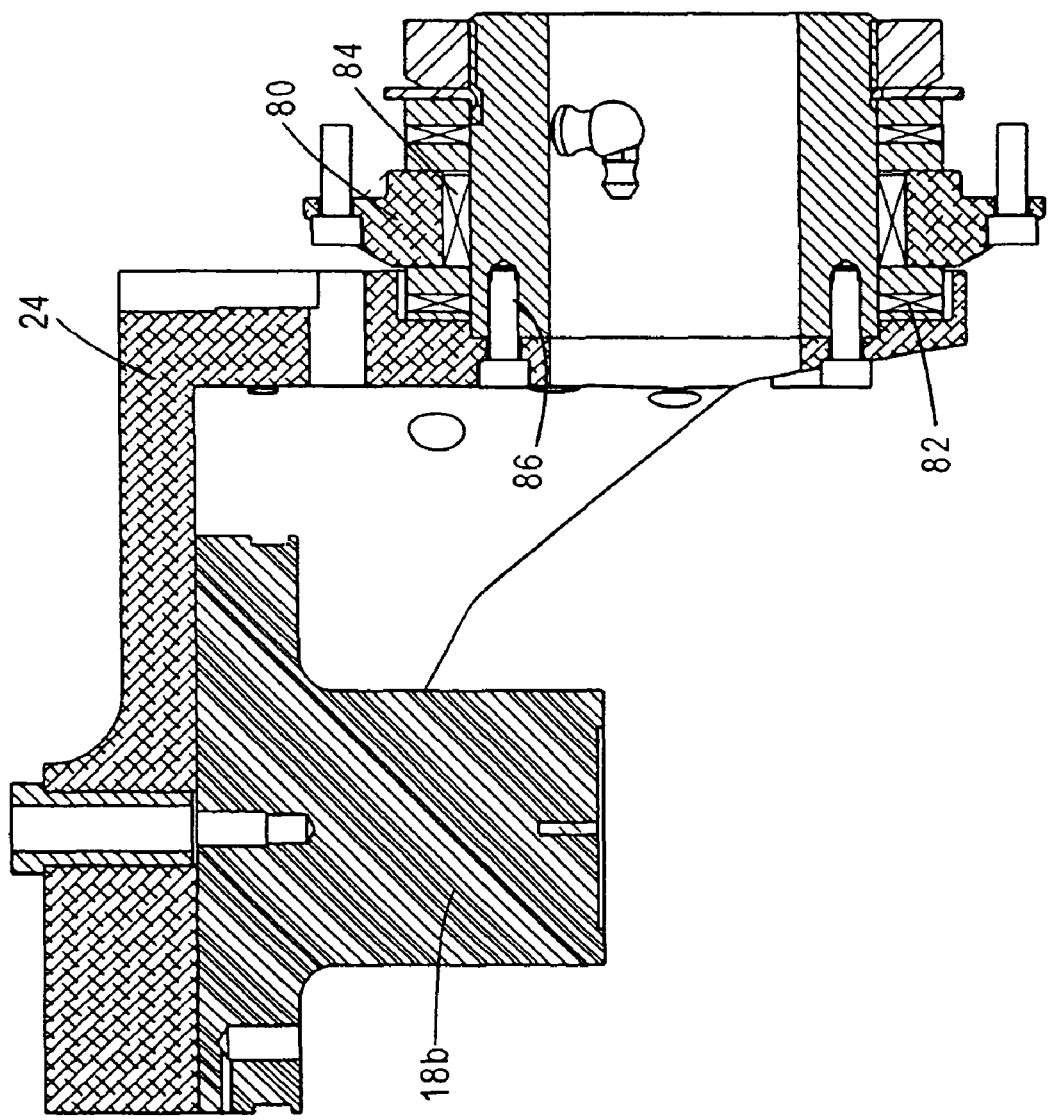
FIG. 13 is a cross-sectional view of a portion of a flexion/extension motion linkage in accordance with embodiments of the invention.

FIG. 13 depicts a cross-sectional portion of the flexion/extension motion linkage. The inner gimbal 24 is depicted as being connected to the upper specimen adapter 18b. A stationary bearing housing 80 houses the needle bearings mentioned before. A radial needle bearing 84 is provided, as well as a needle roller thrust bearing 82, which are provided in two places. A tubular shaft 86 permits rotation of the gimbals 24.

Figure 14:
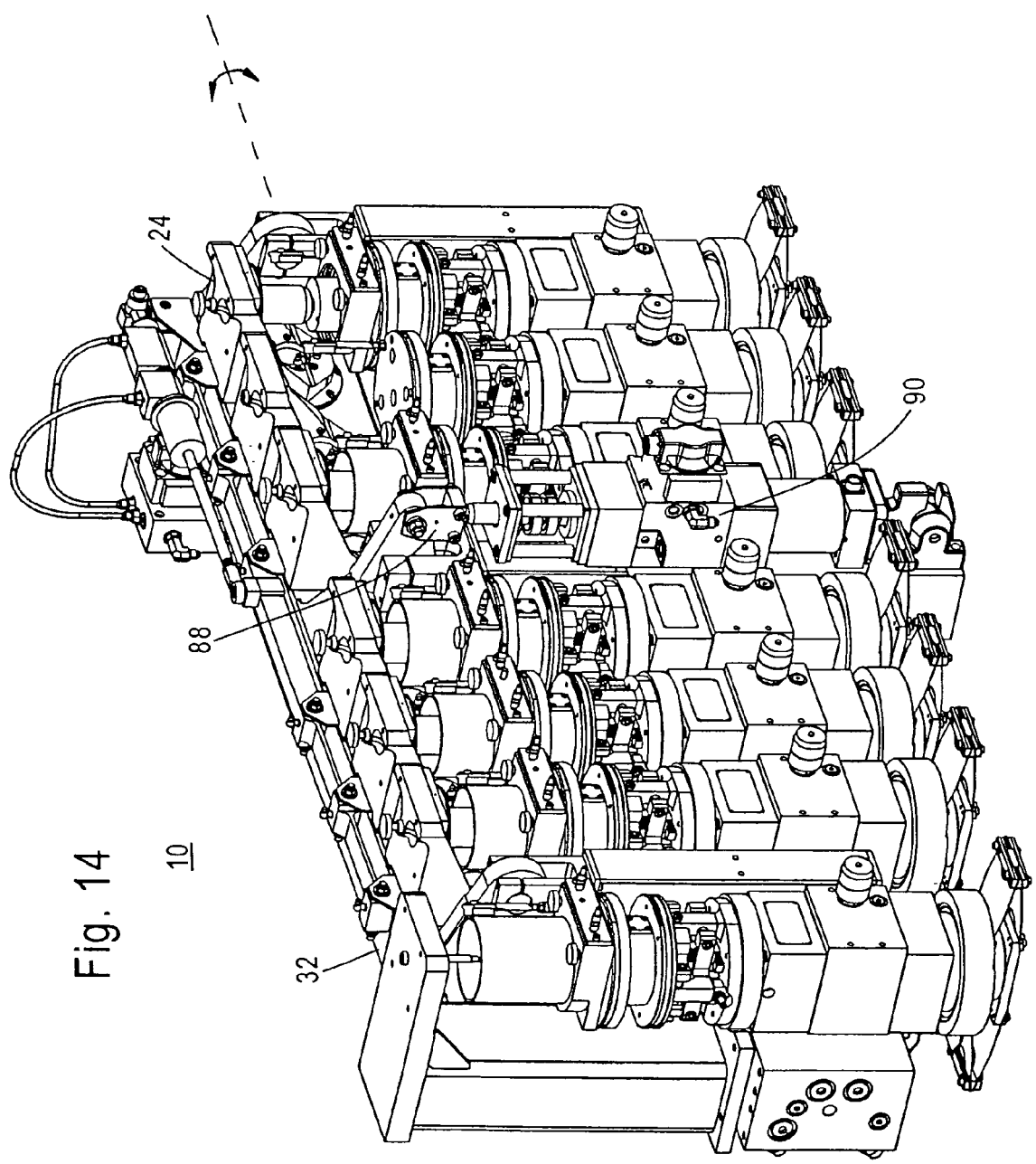
FIG. 14 is a perspective view of the orthopedic simulator of FIG. 1, with an indication of the lateral bending motion around an axis of rotation.

A lateral bending motion around the axis of rotation is depicted in FIG. 14. A moving cross-head 32 (also seen in FIGS. 2a-2d) is coupled via a connecting link 88 that is moved by linear actuator 90 in an up-and-down motion. This causes the inner gimbals 24 to be pivoted around the axis of rotation.

Figure 15:
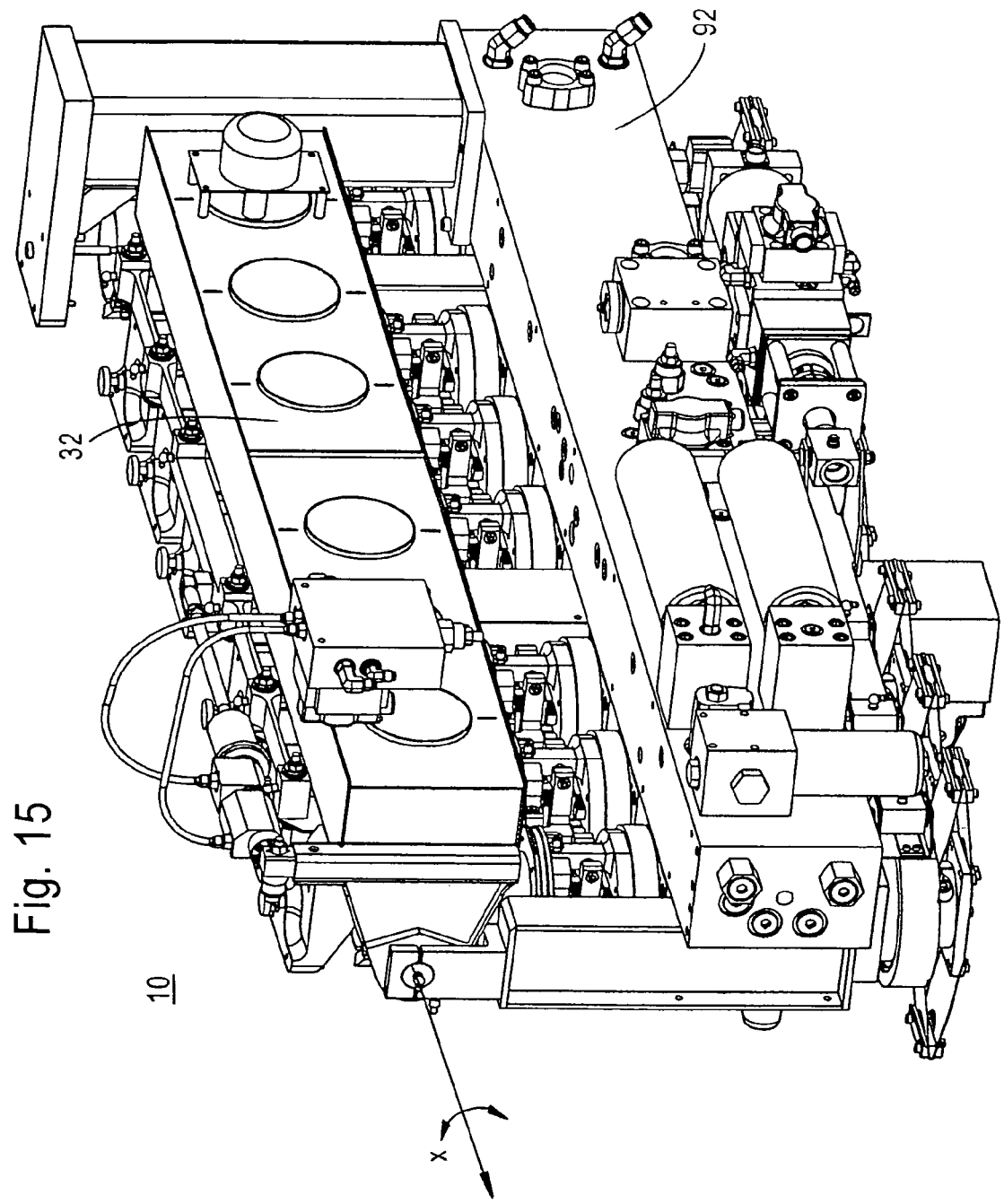
FIG. 15 is a rear perspective view of the orthopedic simulator of FIG. 1.

A rear view of the orthopedic simulator 10 is provided in FIG. 15. The moving cross-head 32 is shown as extending across the orthopedic simulator 10. Also shown in this figure is a central manifold 92, which will be discussed in more detail later. As with the flexion/extension linkages, it is preferred to use long life needle bearings that are of high quality at the key points in the lateral bending motion linkages. These designs ensure long life and low lash, creating an accurate machine for long term use. The low moving mass crosshead assembly maximizes performance. For example, the crosshead assembly 32 may be made of aluminum to provide a very light weight moving mass. In motion, the moving crosshead 32 pivots around the x-axis depicted in FIG. 15.

Figure 16:
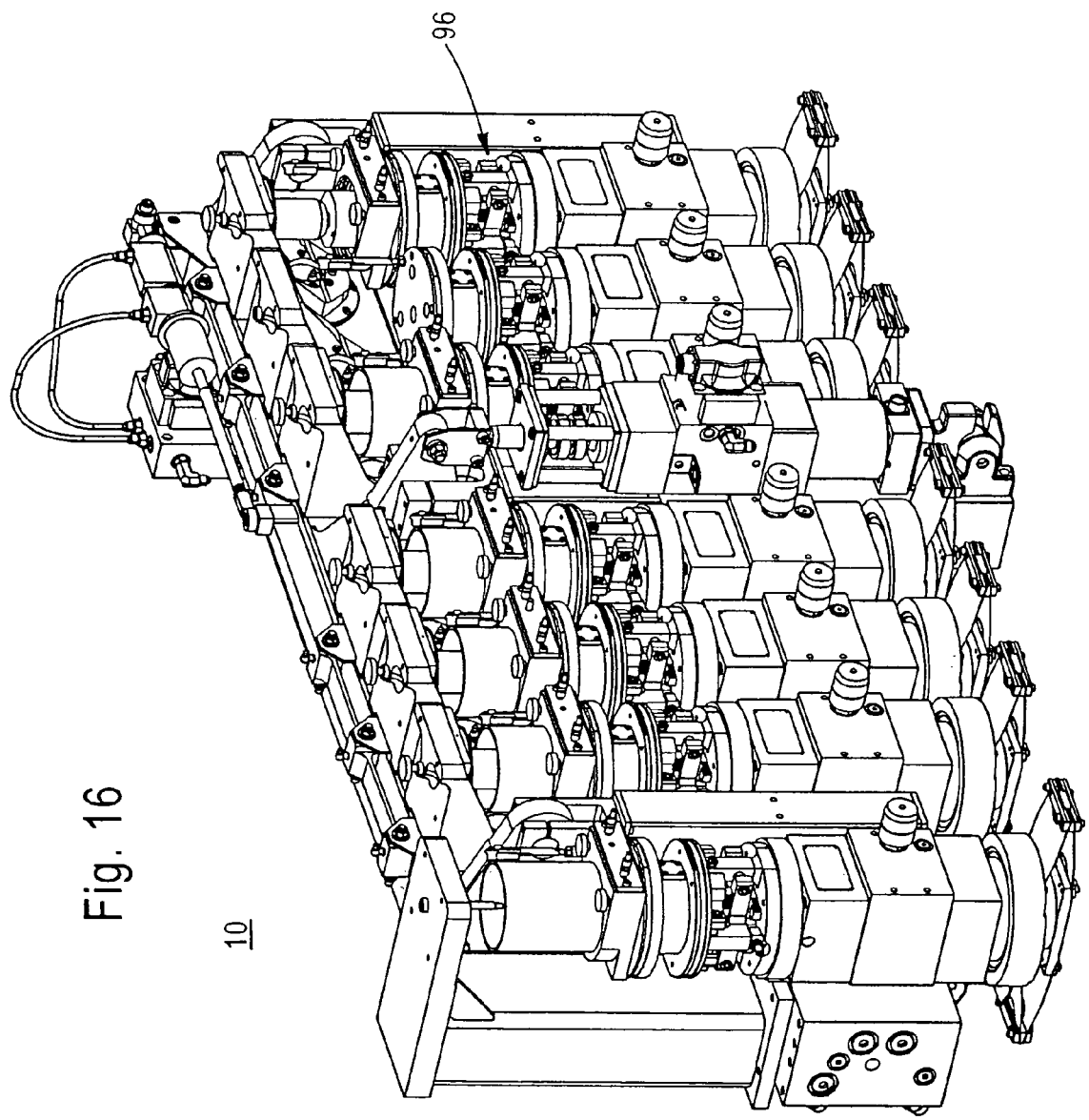
FIG. 16 is a perspective view of the orthopedic simulator of FIG. 1, with an indication of anterior/posterior and lateral translation motions.

FIG. 16 shows the orthopedic simulator and depicts the anterior/posterior and lateral translation motions. A translation stage 96 is illustrated in this drawing. The translation stage includes an x-y slide assembly as will be see in the following figures. FIG. 17 depicts a portion of the x-y slide assembly 100 that shows linear slides 102 with a space 104 being provided for springs that produce a biasing force if desired.

Figure 19:
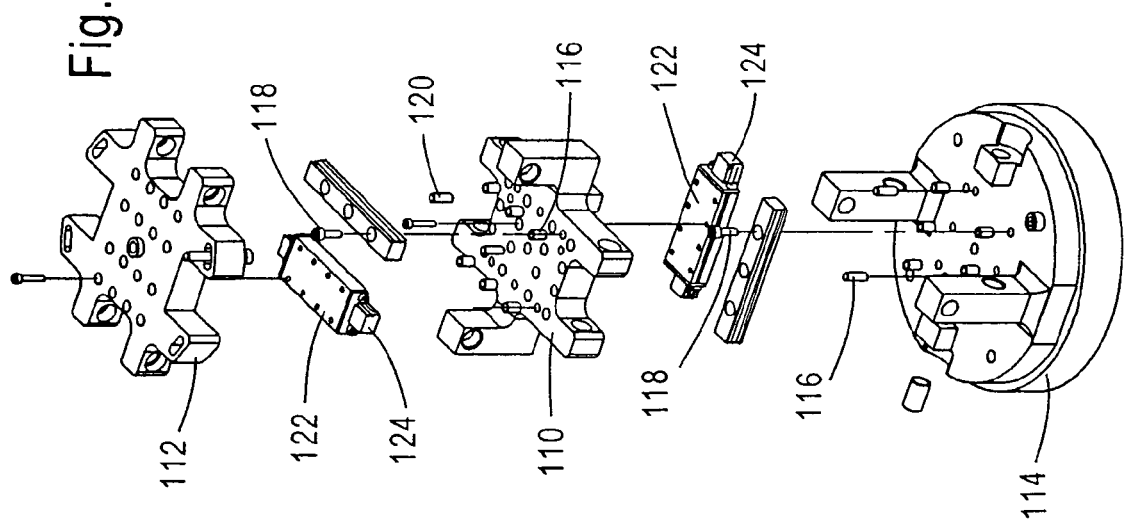
FIG. 19 is an exploded view of the x-y slide assembly of FIG. 18.
Figure 18:
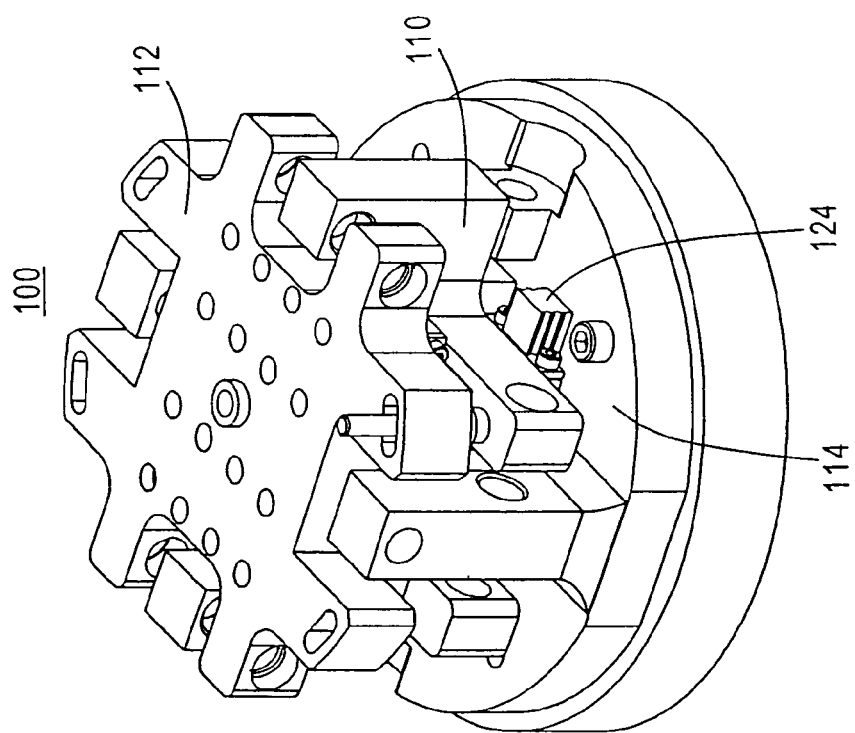
FIG. 18 is a perspective view of the x-y slide assembly in accordance with embodiments of the present invention.

FIG. 18 is a perspective view of the x-y slide table 100 constructed in accordance with embodiments of the present invention. FIG. 19 shows the x-y slide table 100 in an exploded view. The x-y slide assembly 100 forms a very compact package, with a very light weight assembly. There is a high torsion and shear capability of assembly with high axial dynamic load ratings for each x-y slide assembly 100. Each slide assembly 100 also has high moment load ratings, due to its efficient design. There is an ultra-low coefficient of linear static and dynamic friction provided by the design. Double-row/side miniature roller bearings reduce or eliminate fretting corrosion. Lubricant may be provided to assist in the elimination of fretting corrosion and further reduce the coefficient of friction and the start up "stiction."

The x-y slide assembly 100 of the present invention may incorporate three different modes of operation. These include free-floating to self-center a specimen; a positive axis lock within dynamic range; and an ability to produce a high amount of static shear force, on each axis, for simultaneous shear plane loading of specimens. The x-axis transition plate has a built-in capability to align the upper specimen tooling and the load cell radially.

The x-y slide assembly 100 of the present invention overcomes particular concerns. For example, other such assemblies in orthopedic simulators used ball bearings in the slide design which lend themselves to fretting and skidding when translating. Other advantages of the present invention include the production of simultaneous transverse shear in a compact design, while producing friction-free stage floating, but yet is infinitely lockable within a dynamic range. The lowest inertia assembly for Mz rotation is produced, at all six test stations 12. The design of the x-y slide assembly 100 can withstand 1000 plus lbsF in compression. Further, the x-y slide assembly 100 is a translation assembly that can be easily removed from the Fz actuator 26. It also provides a translation assembly that has over-turning moment capability to react moments caused by side loads that are off-centered loading.

The x-y slide assembly 100 includes a lower translation plate 100 and an upper translation plate 112. In certain embodiments, the lower translation plate 110 translates along the x-axis while the upper translation plate 112 translates along the y axis. A base 114 supports the x-y slide assembly and may be mounted on the load cell depicted earlier. Pins 116 are provided and pressed into base 114 and lower translation plate 110. The pins 116 aid in assembly of thee the first mounted slide/rail at each axis and ensures squareness of the first rail to the lock screw post, and establish orthogonality between axis platforms, within the limits of the small screw clearances. Screws 118 are provided, as well as pin dowels 120. Linear rail bearings 122 are provided for linear rails 124.

FIG. 20 depicts the orthopedic simulator 10 and illustrates the loading in the z direction that is provided in the direction of arrows 128 by the vertical load actuator 26. The integral actuator 26 is integral in nature and may be a precision, seal-less actuator design in certain preferred embodiments. The piston rod is floated on an oil film, and the near zero friction maximizes the load accuracy. A low mass rod may be employed to maximize the performance of axial rotation and vertical load channels. The individual test stations 12 have their own on-off valves. A perspective view of an actuator 26 in isolation is provided in FIG. 21. A top view of the actuator 26 is depicted in FIG. 22 and a side view of the actuator 26 is depicted in FIG. 23. A cross-sectional view of the actuator 26 is depicted in FIG. 24.

In certain preferred embodiments, each actuator 26 has a handle 130 on the outside of the actuator 26 that operates a built-in hydraulic valve that allows a user to shut off any station individually. Hence, if a user desires to operate with fewer than six test specimens, or a specimen fails midway through the testing process and it is therefore desirable to remove that specimen from the remainder of the test cycles, the individual test station 12 may be turned off separately from the other test stations 12 without stopping the operation of the machine 10 and the testing of the other specimens. As best seen in FIG. 24, the actuator 26 includes a piston 132 that may be moved axially and rotated. The hydraulic actuator 26 includes a bottom end cap 134 and a top end cap 136. The hydrostatic bearings 138 and 140 are provided. Thrust bearings 142 provide support for a test station 12 when the device is shut off. In such a case, a test station can be removed and the machine operated without the non-operation test station 12 influencing the other test stations 12.

Pressure to extend the piston 132 along the z-axis is provided at port 144, while pressure to retract the piston 132 is provided at port 146.

The hydraulic pressure in return ports 144, 146 are connected to and fed from the central manifold 92 in preferred embodiments. The hydraulic actuator 26 is hydrostatic and is completely without seals, including high-pressure piston seals. The hydrostatic bearings "float" the piston rod and also provide some over-turning moment capabilities. The unique design produces an actuator without seal drag (as in a typical hydraulic actuator), resulting in a device that has extremely low linear and torsional friction. The only friction is the friction that is produced from viscous oil shear. With this design, an equal Fz force is provided across all seven actuators.

Thrust bearings are provided in the end of each end cap 134, 136. The upper end cap 136 has thrust bearings lubricated by a blow-by actuator rod oil leakage. If one specimen should fail before others, an operator can turn off the station 12. The actuator 26 retracts and the assembly will ride on the thrust bearings for a continued Mz motion. The Mz motion is common for all six Fz actuators 26 at the six test stations 12. The seventh test station 14, which operates as a load and soak station for control purposes, is not connected to the Mz drive apparatus.

Figure 26:
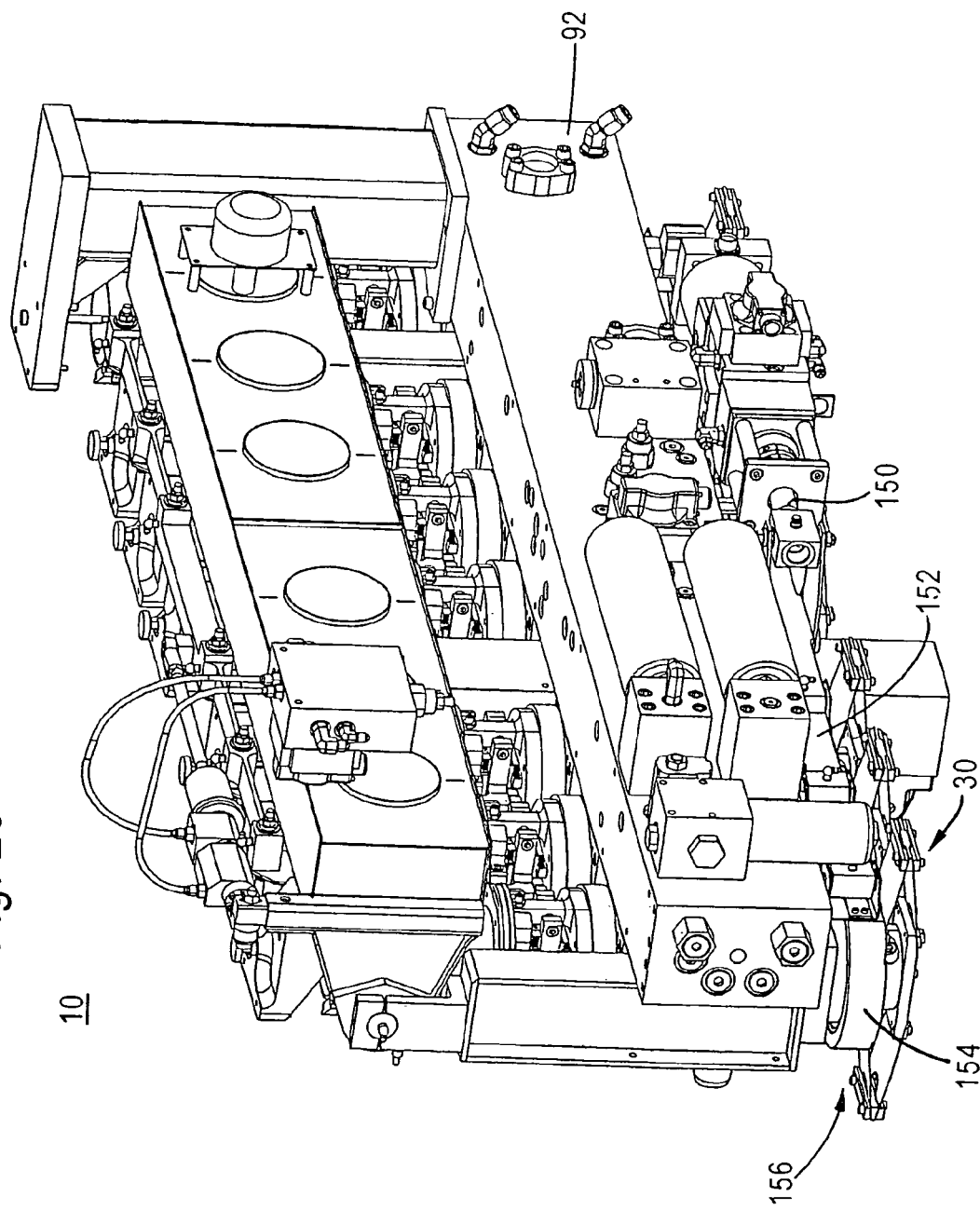
FIG. 26 is a rear perspective view of the orthopedic simulator of FIG. 1, illustrating an embodiment of a central manifold in accordance with embodiments of the present invention.

The central manifold 92, depicted, for example, in FIG. 26, provides an integral manifold for multiple connections and fluid tubing for the orthopedic simulator. The use of a central integral manifold greatly reduces plumbing, provides a performance improvement since there is a greater balancing of fluid and less plumbing is required, a size reduction, a cost reduction and also serves as a structural element. In other words, the central manifold 92 provides a strong cross-brace for the orthopedic simulator 10. Examples of the plumbing include providing the fluid to the extension and retraction fluid connections of the vertical load actuators 26. The central manifold 92 also provides for lubrication fluid circulation.

Figure 35:
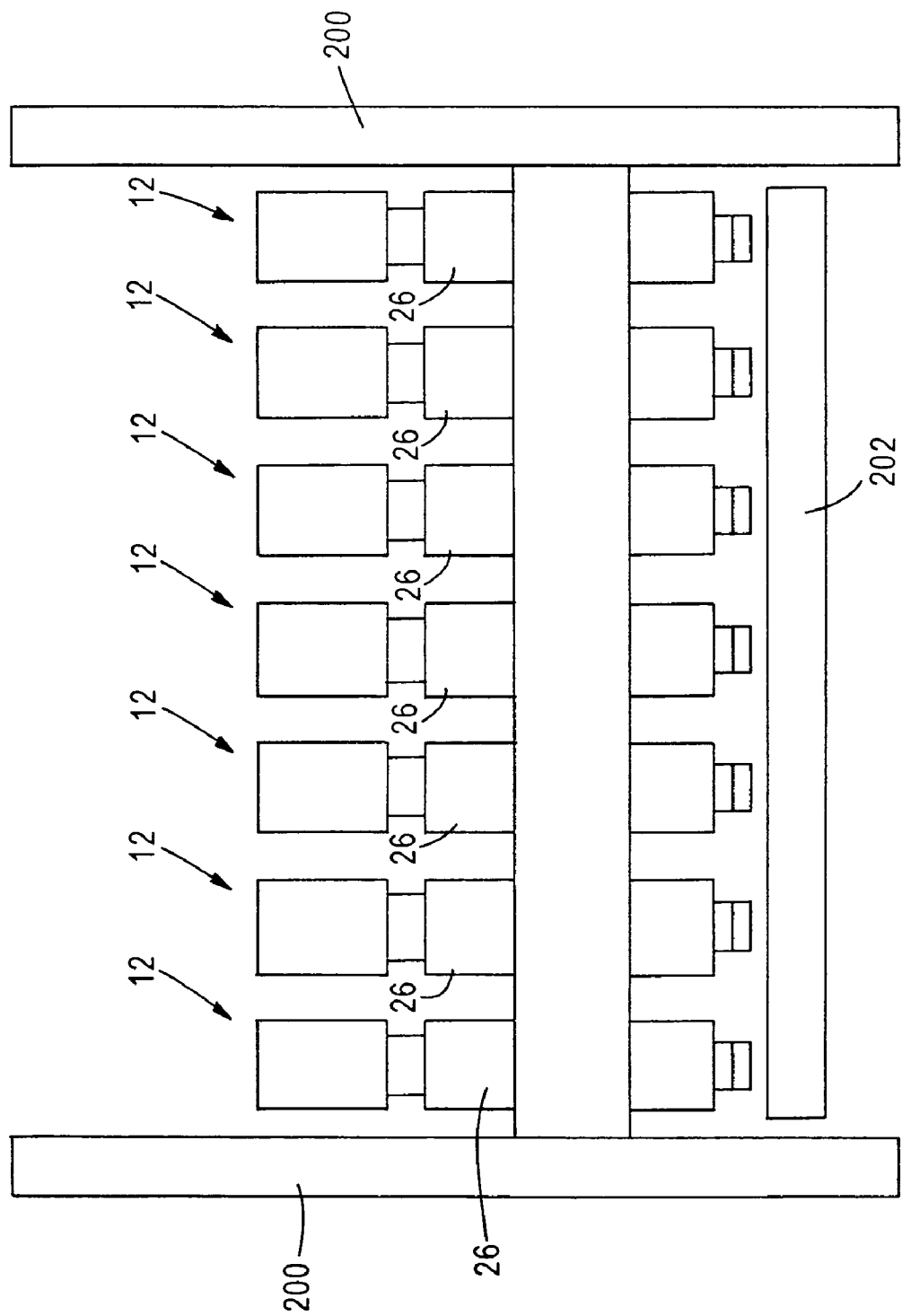
FIG. 35 is a rear schematic view of the orthopedic simulator and the central manifold in accordance with embodiments of the invention.

A schematic depiction of the central manifold 92 installed as a structural element is provided in FIG. 35. The manifold 92 spans the test stations 12 and is structurally coupled to, for example, a pair of vertical supports 205. The central manifold 92, coupled in this manner, can thereby serve as a cross-brace for the orthopedic simulator 10. This will reduce the effect of vibrations during the testing operation. Although a pair of vertical supports 205 is illustrated, the vertical supports 205 are exemplary support elements only, as the central manifold 92 may be structurally coupled to other structural and support elements of the orthopedic simulator 10, such as the walls of the external housing for the orthopedic simulator 10 Further, presently preferred embodiments of the invention employ three vertical supports 205 to which the central manifold 92 is coupled. Also schematically depicted in FIG. 35 is a sump system 202 into which operating fluid is collected, and which will be discussed later.

Figure 36:
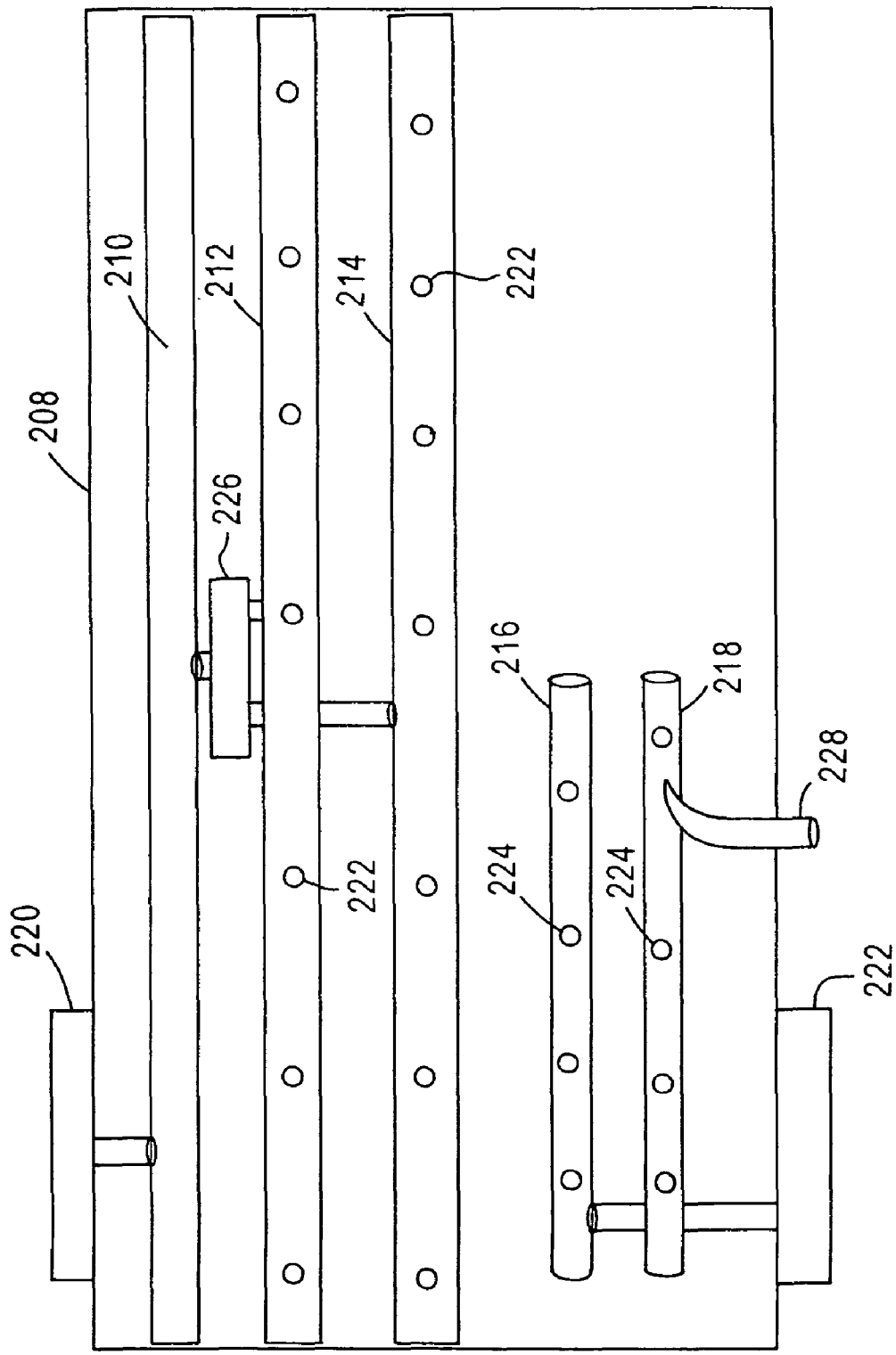
FIG. 36 is a schematic internal view of an exemplary embodiment of the central manifold.

A basic cross-sectional depiction of an embodiment of the central manifold 92 is provided in FIG. 36. This embodiment is exemplary only, as other internal connections and tubing arrangements are provided in different embodiments, depending on the particular configuration of the orthopedic simulator 10. Certain details are not illustrated so as not to obscure some of the inventive aspects. For example, a number of valves and connections may be provided, but are not illustrated.

Figure 37:
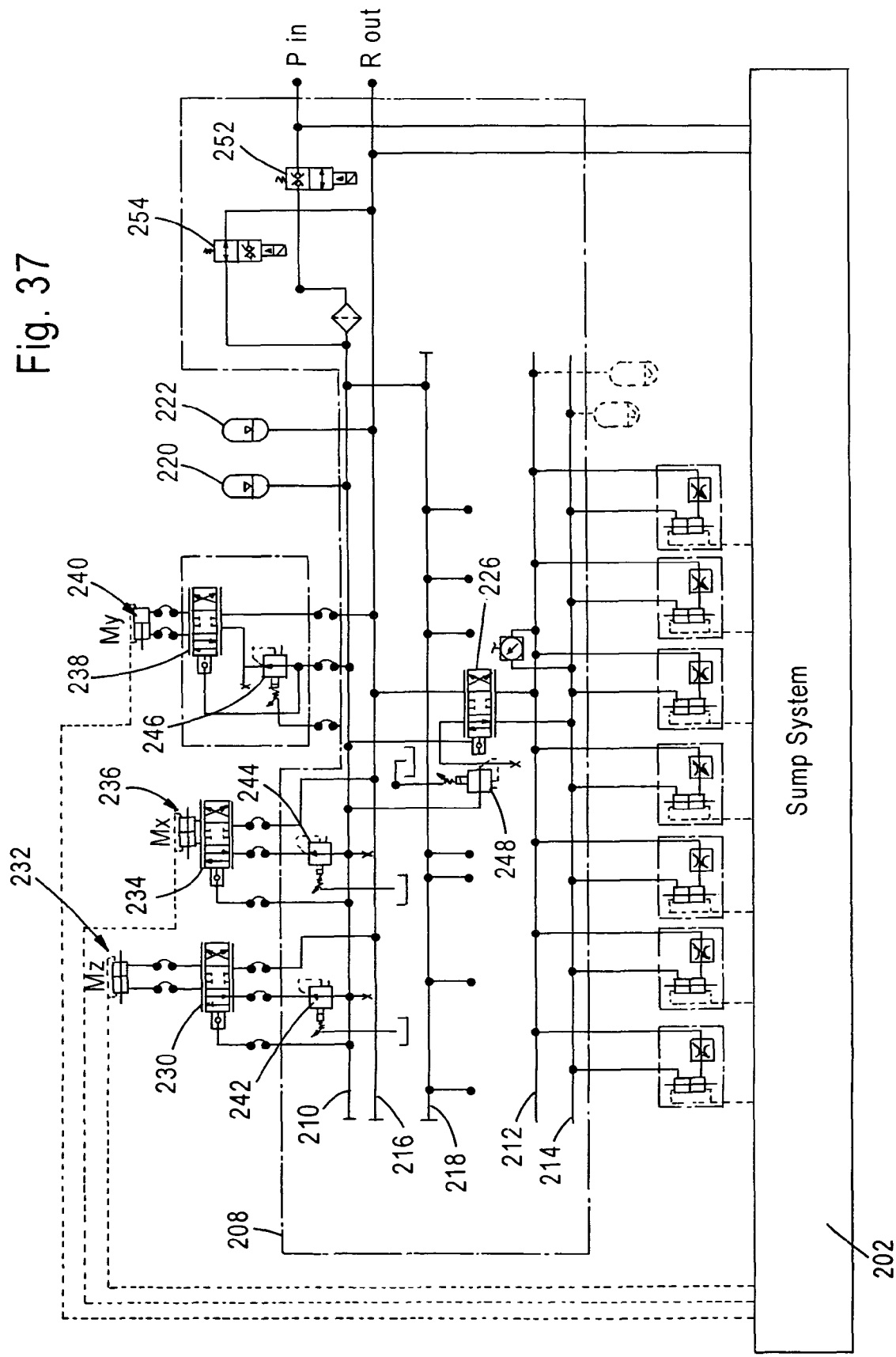
FIG. 37 is a schematic of an exemplary hydraulic circuit of the orthopedic simulator.

In describing the central manifold 92, reference should also be made to FIG. 37, which is a schematic diagram of a hydraulic system for the orthopedic simulator 10. Again, this is an exemplary embodiment only, as other configurations of the hydraulic system may be employed depending on the particular arrangement and needs of the orthopedic simulator 10. Furthermore, the configuration of the orthopedic simulator 10 to operate with a hydraulic system and the configuration of the central manifold 92 to accommodate the hydraulic connections is exemplary only. In certain other embodiments, the orthopedic simulator 10 operates on pneumatics, and in other embodiments, is an electric system. The central manifold 92, in such embodiments, is configured to accommodate the pneumatic or electrical connections. In an electrical system, the central manifold 92 can serve as an integral heat sink and structure and also serve as a portion of an actuator itself. Surface mount components can be mounted directly to the central manifold 92. Although these other systems are within the scope of the present invention, the following description is cast in terms of a hydraulic system.

The central manifold 92, in certain embodiments, comprises a manifold housing 208 that is formed from a substantially solid block of material. For example, the manifold housing 208 may be formed from a solid block of aluminum or other appropriate metal. However, different materials may be used, though it is preferred to provide the structural reinforcement capability discussed earlier for the material to have a high rigidity. In certain embodiments, the manifold housing 208 is not formed from a substantially solid block of material, but rather is hollow and formed by a number of walls enclosing a space. The reinforcing capability may be compromised to some extent by being a hollow housing, but in certain applications, the amount of reinforcement provided by such a structure may be sufficient.

A number of fluid tubes are provided in the manifold housing 208. When the manifold housing 208 is formed from a substantially solid block of material, the tubes and connections between the tubes may be created by appropriate drilling or other methods. A switched pressure tube 210 carries pressurized hydraulic fluid for distribution to the various actuators. The switched pressure tube 210 provides the hydraulic fluid to operate Mz actuator 232 through a servo valve 230. An example of an Mz actuator 232 is the linear actuator 150 in FIG. 26, although types of Mz actuators may be employed. Similarly, the Mx actuator 236 is provided with hydraulic fluid through servo valve 234, and My actuator 240 is provided with hydraulic fluid through servo valve 238.

A second switched pressure tube 218 is formed within the manifold housing 208 and contains fluid inlets 224. The second switched pressure tube 218 is coupled to the switched pressure tube 210 and provides additional pressure points.

A return collector tube 216 is provided that is connected by fluid inlets 224 to the servo valves 230, 234, 238. It is also connected to ganged servo valve 226, which will be discussed in more detail below. The return collector tube 216 receives return hydraulic fluid from the servo valves 226, 230, 234 and 238. The hydraulic fluid is returned to the sump system 202.

An on/off valve 252 connects a source of pressurization to the switched pressure tube 210. A dump valve 254 allows fluid to be provided from the switched pressure tube 210 to the return collector tube 216. A time delay based on the operation of the on/off valve 252 may be utilized to control the dump valve 254.

An accumulator 220 is coupled to the switched pressure tube 210, and another accumulator 222 is coupled to the return collector tube 216. The accumulators 220, 222 store hydraulic energy and make this energy available again to the system as necessary.

The switched pressure tube 210 provides hydraulic pressure to a first operating pressure tube 212 and a second operating pressure tube 214. The hydraulic pressure is provided through the ganged servo valve 226, under the control of the pressure control valve 248. The plurality of Fz actuators 26 are have extension and retraction ports coupled respectively to the first operating pressure tube 212 and the second operating pressure tube 214 through the fluid outlets 222 (shown in FIG. 35). Hence, operation of the Fz actuators 26 is controlled by pressurization provided through the first and second operating pressure tubes 212, 214. Hydraulic fluid is allowed to drain into the sump system 202 from the Fz actuators 26.

The first and second operating pressure tubes 212 and 214 have relatively wide diameters, in certain embodiments, to provide low loss. It is desired to make the plurality of Fz actuators 26 self-balanced, such that they experience the same pressure. To achieve this, in certain embodiments, all the chains from the servo valve 226 to each of the Fz actuators 26 are made as common as possible. The servo valve 226 is physically located in the middle of the Fz actuators 26, in order to compensate to the greatest extent for different distances from the inlet of the pressurized fluid.

The routing of all of the hydraulic connections in the central manifold provides an improved balancing of the hydraulic fluid in the system. As well, reductions in size and cost are achieved. When attached to other structural elements of the orthopedic simulator 10, the central manifold 92 provides a reinforcing function, so as to resist and transfer bending and shear forces to the vertical supports. This is beneficial in solidifying the simulator 10, helping to quiet vibrations and improve testing consistency and accuracy. The central manifold 92 can also be configured, as discussed earlier, to provide routing for pneumatic or electrical connections in certain embodiments, or some combination of hydraulic, pneumatic and electrical connections. Hence, the central manifold 92 can be considered to contain operating power transmission carriers of different types, such as hydraulic fluid tubing, pneumatic tubing, or electrical wiring, depending on the type of actuators that are employed. Whichever connections are provided, the central manifold 92 achieves the structural purpose of resisting and transferring bending and shear forces in addition to making the machine more compact.

Figure 25:
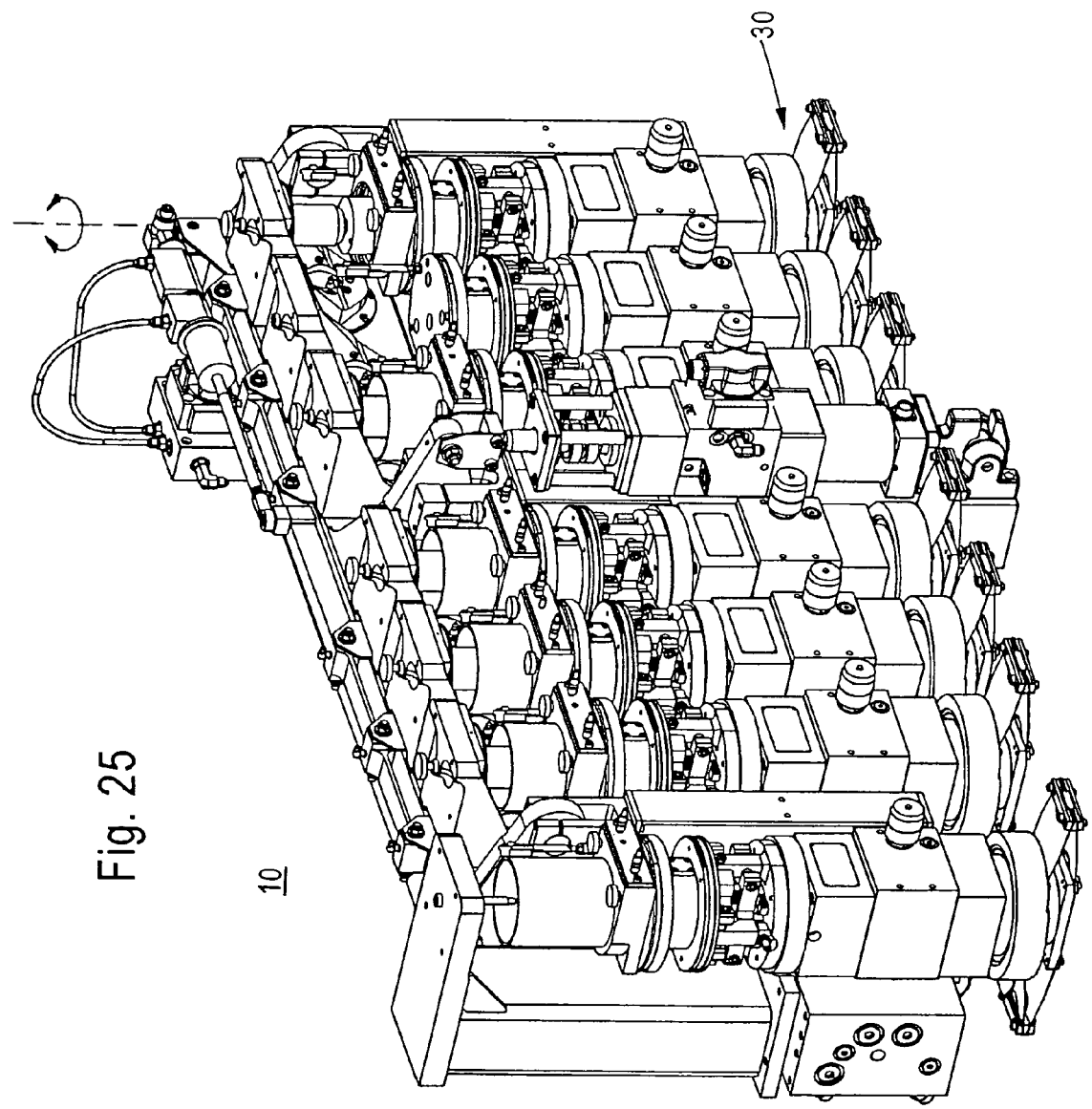
FIG. 25 is a perspective view of the orthopedic simulator of FIG. 1, with an indication of the axial rotation linkage and a moment provided at a test specimen.

FIG. 25 shows the orthopedic simulator 10 and highlights the axial rotation linkage 30 originally shown in FIG. 1. The axial rotation linkage 30 provides a moment Mz at the test specimen. Referring now to FIG. 26, which shows a rear view of the orthopedic simulator 10, a linear actuator 150, via connecting link 152, provides the driving force that causes the axial rotation linkages 30 to rotate around the z-axis.

It is desirable to provide a transmission of drive torque with little deflection related error, having high torsional stiffness. At the same time, low axial stiffness is desirable so that there is little cross-talk onto the vertical loading end and so that cross-talk is not seen at the load cell. The axial rotation linkage includes a rotational transfer link 154 that is coupled to the connecting link 152. Movement of the connecting link 152 in a linear fashion causes the rotational transfer link 154 to freely rotate on bearings around the z-axis. A flexure assembly 156 that is torsionally stiff but axially compliant is coupled to the bottom of the piston 132 of the vertical load actuator 26. The flexure assembly is torsionally stiff so as to rigidly transfer torque between the rotational transfer link 154 and the piston 132 of the actuator 26. A friction free axial/torsion actuation is provided by the combination of the actual rotation linkage 30 and the friction-free vertical force actuator 26. In operation, the vertical load actuator 26 applies a load to the test specimen 40 along the z-axis by moving the piston 132 along the z-axis. Driven by linear actuator 150 through the connecting link 152, the rotational transfer link 154 and the flexure assembly 156 facilitate rigid torque transfer to the piston 132 to the test specimen (not shown) at one of the test stations 12. The piston 132 is allowed to translate along its axis freely due to the high axial compliance provided by the flexure assembly 56 of the axial rotation linkage 30.

Figure 27:
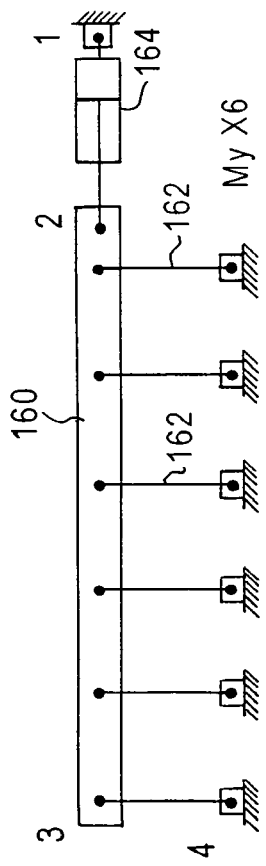
FIGS. 27-29 schematically depict different approaches to linkages.
Figure 28:
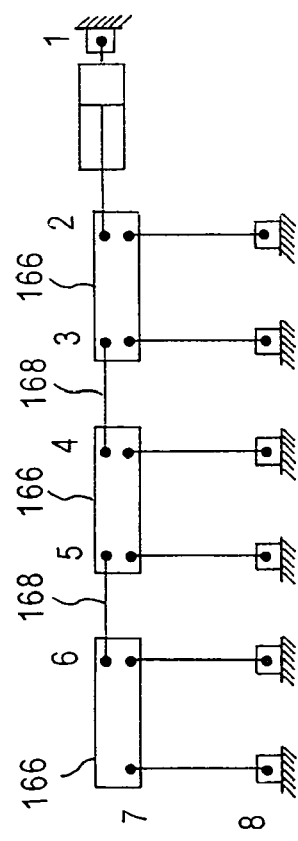
Figure 29:
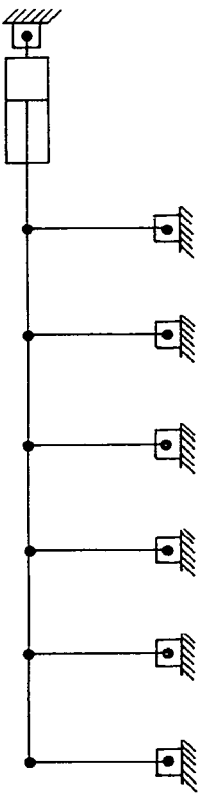

FIGS. 27-29 depict linkage approaches and highlight the differences between embodiments of the present invention and alternate linkage approaches which provide greater joint serialization error. In FIG. 27, a common sublinkage is provided for the flexion/extension (My) and axial rotation (Mz) to thereby create the fewest common number of joints between each specimen, between the displacement measuring device and each specimen, and between the drive actuator and each specimen. In this manner, variability is minimized. The approach provided in the present invention is depicted in FIG. 27. As can be seen, the solid cross-piece 160 provides force to all the linkages 162 at once, from the actuation mechanism 164. By contrast, FIG. 28 employs three separate connecting bars 166 which are connected by two links 168. Hence, those test specimens at the left side of FIG. 28 have a larger number of joints (8) than the number of joints (4) for the left-most specimen in FIG. 27. This increases the variability in the forces and motions applied to the test specimens from test station to test station. A similar variability is provided in FIG. 29, in which a large number of joints are provided for the various test stations, with each test station having a different number of joints. Hence, the arrangement of the present invention reduces variability in force and motion application from test station to test station.

Figure 30:
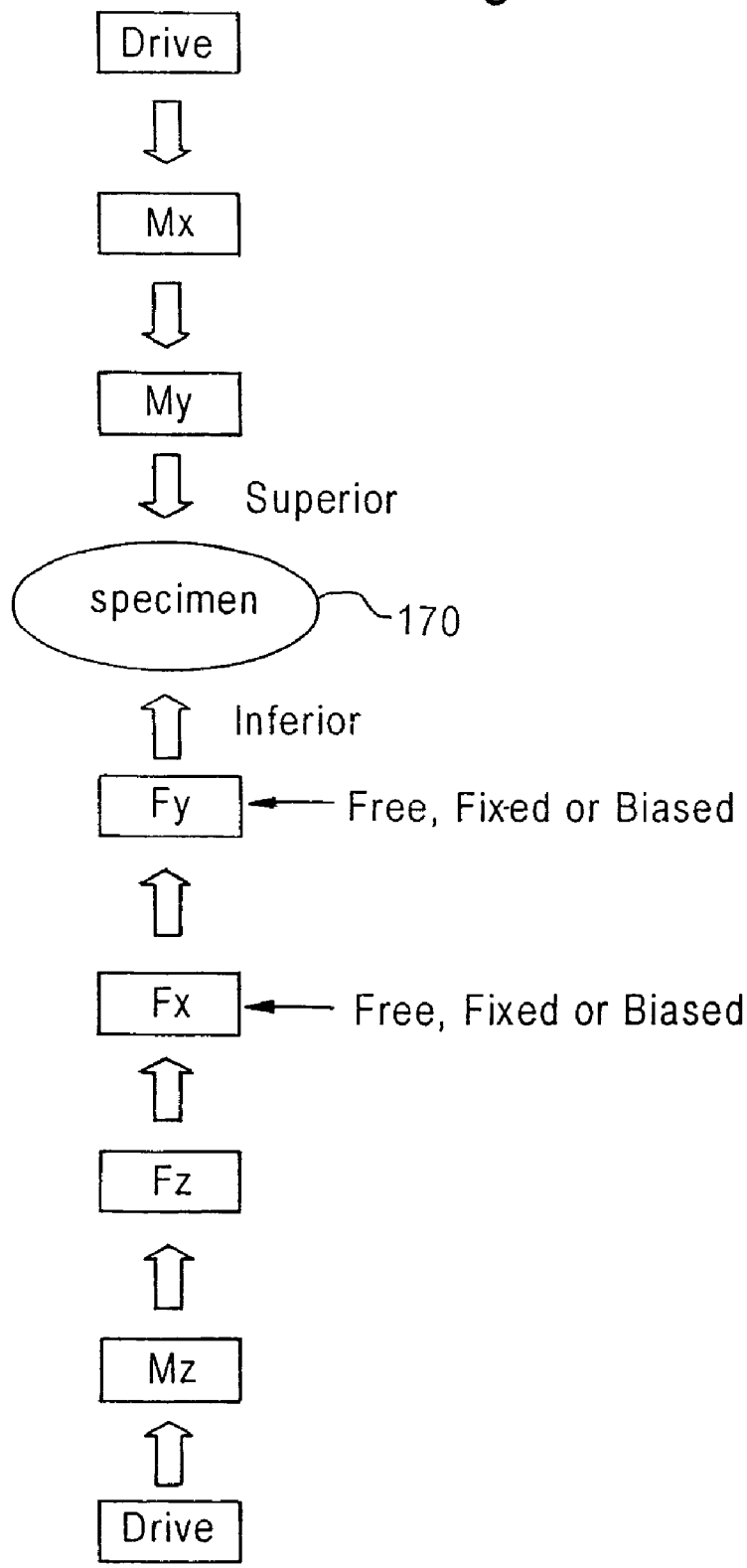
FIG. 30 schematically depicts a nesting order of forces in accordance with embodiments of the present invention.

FIG. 30 schematically depicts the nesting order of forces in accordance with embodiments of the present invention. This nesting order of forces is achieved by the arrangement of the linkages as depicted in the figures throughout this application.

The mechanism system generates relative motions and forces between the lower (inferior) and upper (superior) portions of orthopedic devices, such as multiple intervertable disc implants, simultaneously to generate wear on the artificial bearing surfaces over similar motion and force induced degradation with time. The mechanism applies these motions and forces in such a way as to maximize the accuracy, test speed and durability of the linkage. The full six degree of freedom linkage system is nested as shown in FIG. 30 to maximize performance and accuracy. Typical spinal implant tests in conventional systems require higher displacements in the flexion/extension direction (My), as compared to the lateral bending (Mx) and axial rotation (Mz) rotations. These motions are often performed at a common or similar frequency and wave shapes. Therefore, the flexion/extension motion represents the most demanding performance. The mechanism system of the present invention is nested, however, so as to place the sub-mechanism with the highest required performance closest to the specimen. This thereby minimizes the moving mass and any related inertial induced error. Hence, as seen in FIG. 30, the schematically induced specimen is indicated by reference numeral 170. The closest sub-mechanism to the superior (upper) portion of the test specimen 170 is the flexion/extension (My). The lateral bending (Mx) is further from the superior portion of the specimen 170, as indicated by FIG. 30. Finally, the drive for the Mx and My forces is furthest away from the specimen 170. For the lower (or inferior) portion of the specimen 170, the force in the y direction is free, fixed or biased and has a minimized moving mass and has the highest required performance. The forces in the x direction Fx is then nested further from the specimen 170 than the Fy force. The vertical force provided by the actuator 26, Fz, is still further from the inferior portion of the test specimen 170, with the moment around the z-axis, Mz, being provided in a nesting arrangement still further from the test specimen 170. The drive for all these forces is provided as indicated.

The Euler sequence of rotational motion as applied by the mechanism of the present invention is flexion/extension->lateral bending->axial rotation. In the field of testing of spinal implants, this ordering of the mechanism promotes maximum performance and minimizes the additive joint error. The independency of linkages reduces or eliminates cross-talk and allows accurate control of the phases between the individual mechanisms. This is important to create the desired and controlled loading of the test specimen 170.

Figure 31:
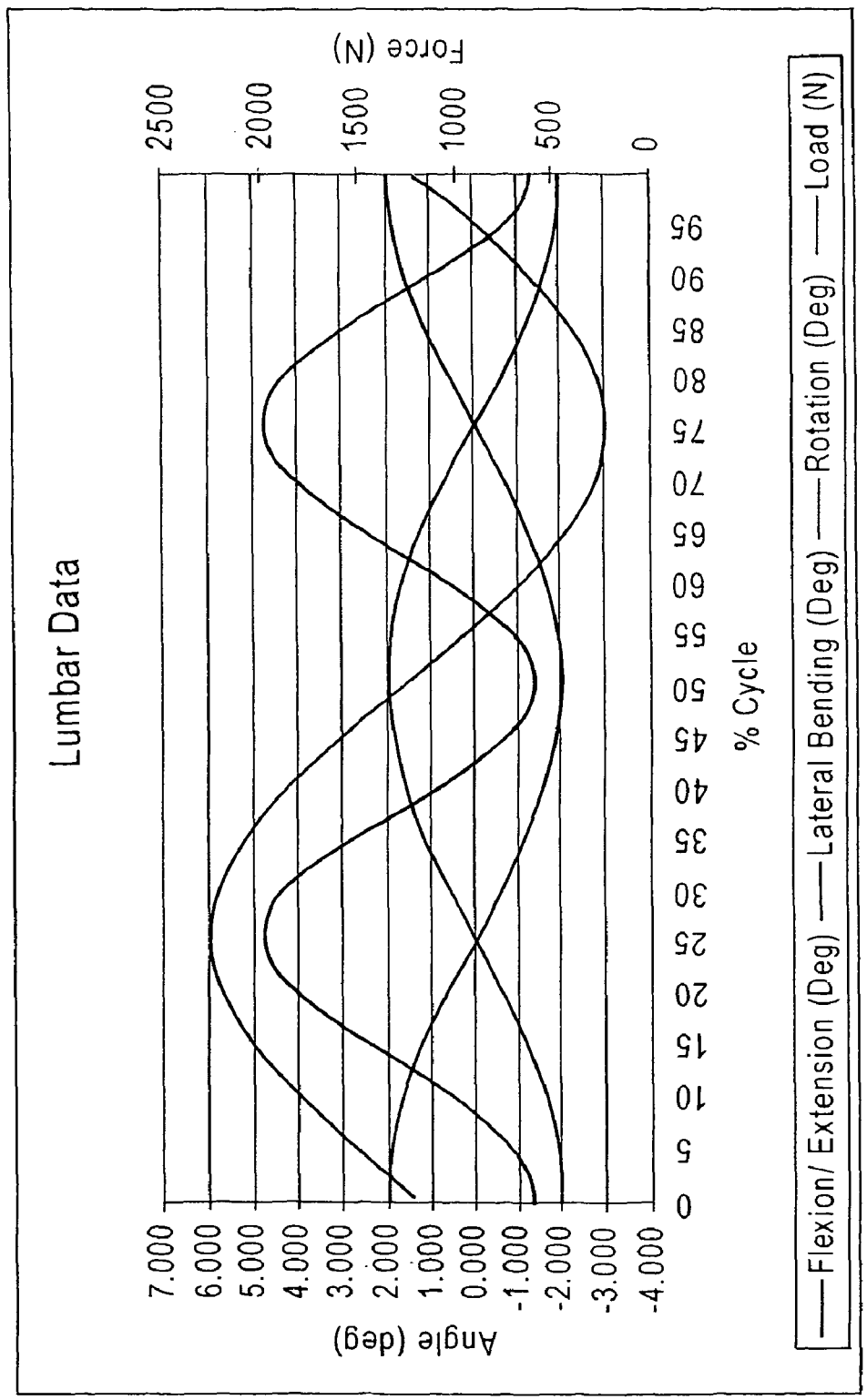
FIG. 31 shows the required forces for application to a test specimen intended for a lumbar region according to an exemplary set of curves.
Figure 32:
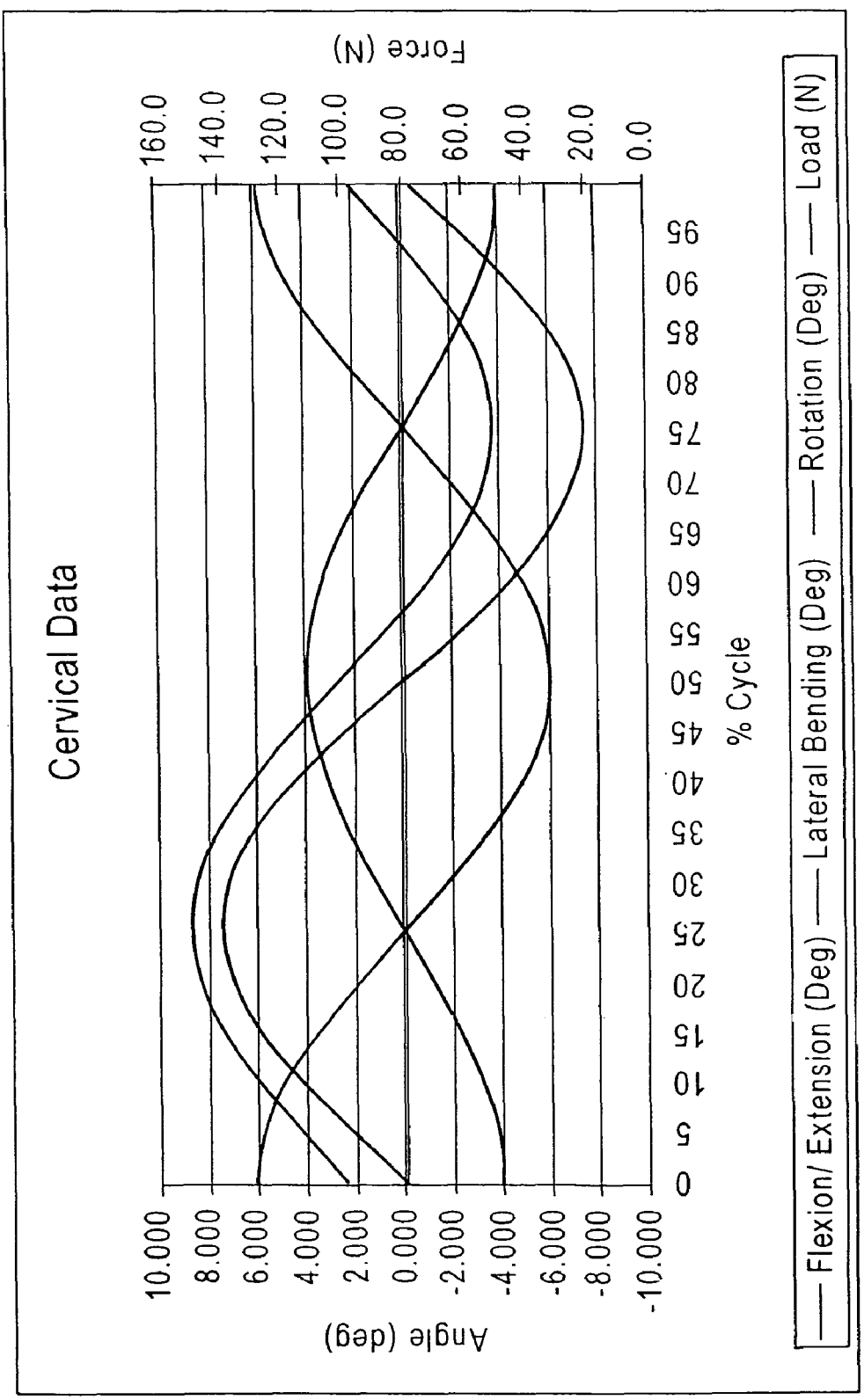
FIG. 32 shows the same information as FIG. 31, but for cervical data.
Figure 33:
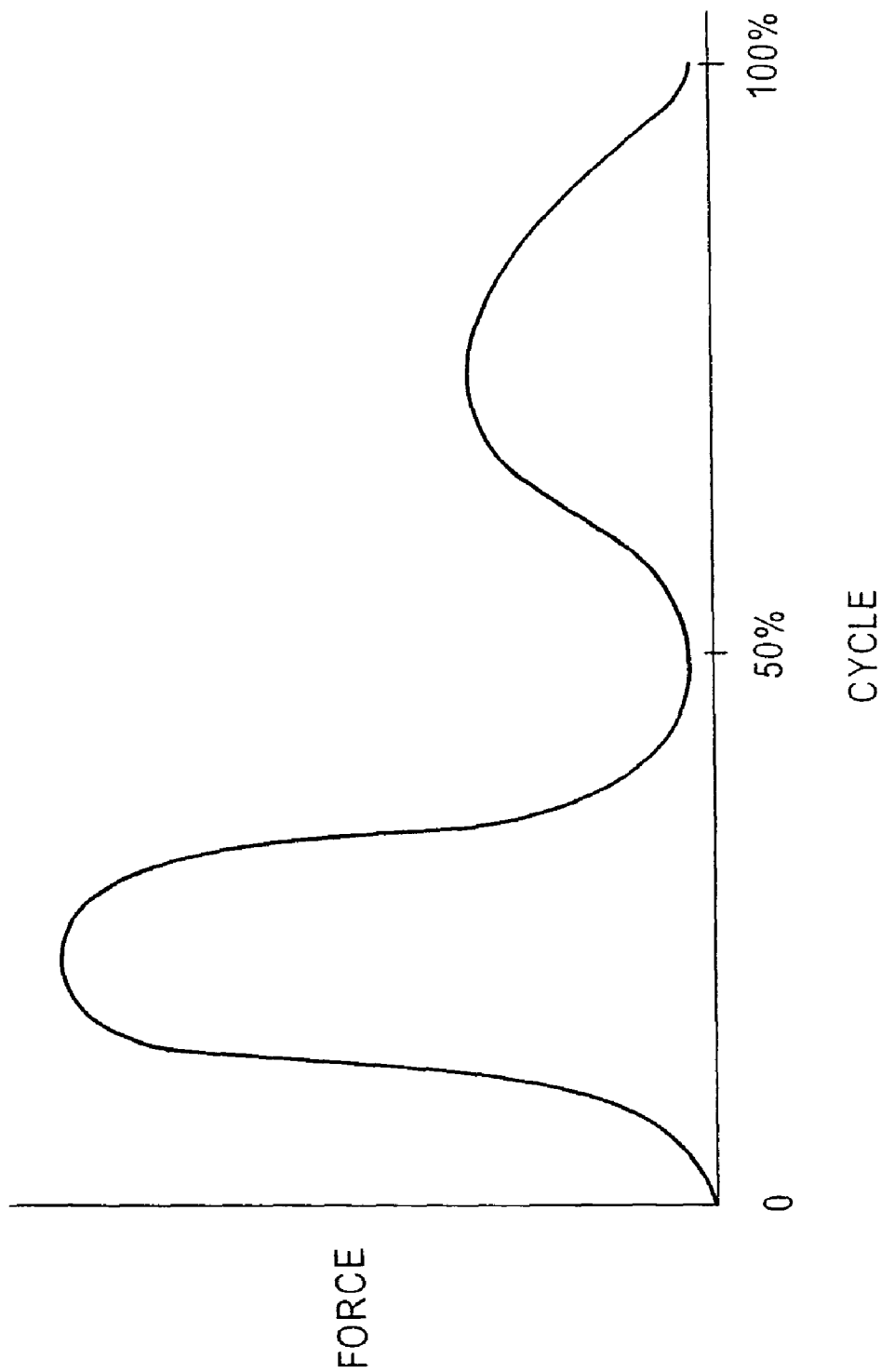
FIG. 33 shows curves for non-sinusoidal input data in accordance with exemplary embodiments of the invention.

FIG. 31 shows the required forces for applying to a test specimen of a spinal implant intended for the lumbar region according to the an exemplary set of curves. Similarly, FIG. 32 shows the same information for cervical data. Duty cycle loading involves inserting high loads and displacement activity into a more typical repeating activity, such as lifting a heavy box periodically. This allows for the insertion of periodic overload states. Such overload states are known to potentially induce damage, but are relatively rare so that their rarity should be considered and the overload states placed in the context of other daily activity when included. In addition to duty cycle loading, embodiments of the present invention provide for re-creating any sinusoidal or non-sinusoidal curve, which allows for more accurate simulation (e.g., a "walking simulation"). The embodiments of the invention allow for inputting non-sinusoidal data with varying phase, amplitude and frequency content, such as real walking profiles. These curves, such as shown in FIG. 33, can be repeated for a large number of cycles, and hence are fatigue or wear generating. The representation of activity is not limited to walking, as one of ordinary skill in the art will readily appreciate, but may be used to simulate any number of replicated activities in a serial or repetitive fashion. Accordingly, a controller 200, seen only in FIG. 1, is used to independently and individually control each of the motion devices. Hence, the flexion/extension, lateral bending, rotation, and loading of the test specimen 170 may be controlled to any desirable curve through the use of control software and the mechanisms provided in the orthopedic simulator 10. This allows for the testing of an orthopedic device that simulates actual conditions that the orthopedic device will be subjected to rather than the constant forces depicted in FIGS. 31 and 32 applied over 10 million cycles. For example, a test may account for the typical day for humans. Such a day may include sitting for hours at a time with intermittent periods of activity, including walking and sleeping periods. Strenuous physical activity, such as for athletes, may also be better modeled. The controller 200 thereby more accurately causes the orthopedic simulator 10 to simulate the forces that a spinal implant or other orthopedic device will actually be expected to see for a typical implant recipient.

Figure 34:
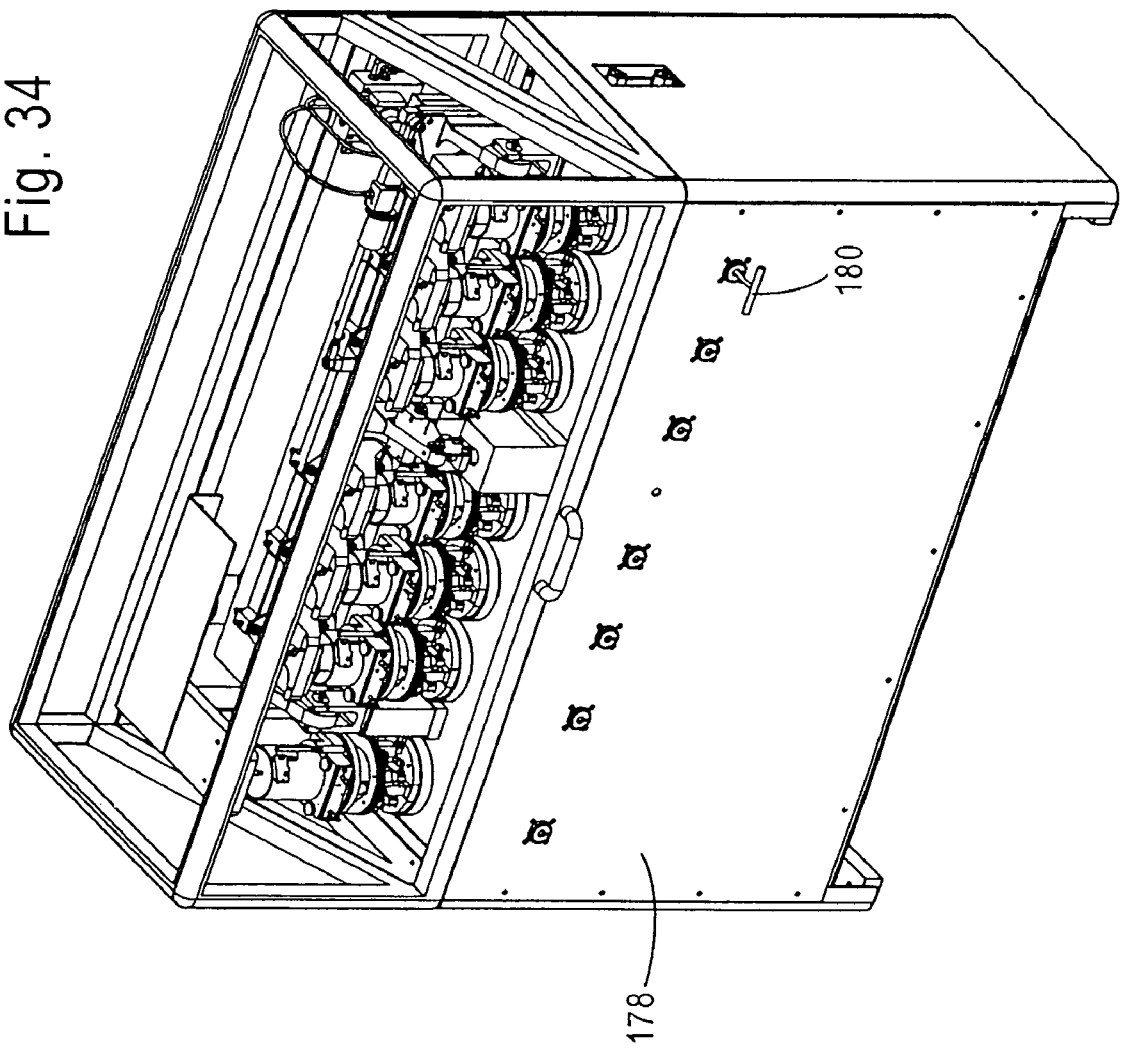
FIG. 34 depicts the orthopedic simulator within a housing.

FIG. 34 depicts the orthopedic simulator 10 within a housing 178. The use of a housing 178 prevents contamination and reduces oil within the environment. Switches 180 allow a test station to be shut down very quickly in order to prevent invalidating of a test if an individual test station 12 should experience difficulty in operation.

Although the present invention has been described and illustrated in detail, it is to be clearly understood that the same is by way of illustration and example only and is not to be taken by way of limitation.

What is claimed:

1. An orthopedic simulator comprising:
a frame including at least one support and the at least one support including a first portion and a second portion spaced from the first portion;
at least one holder assembly including an upper adapter and a lower adapter configured to hold a test specimen;
a plurality of actuators coupled to the at least one support of the frame to supply a load or force to the test specimen through at least one of the upper or lower adapters; and
an integral manifold including at least one passage and the plurality of actuators are coupled to the least one passage of the integral manifold to supply the test load or force and the upper adapter being coupled to the first portion of the at least one support and the lower adapter being coupled to the second portion of the at least one support through the integral manifold coupled to the second portion of the at least one support to form a load element to resist and transfer loads or forces.

2. The simulator of claim 1, wherein the integral manifold is a substantially solid block of material forming a manifold housing and the at least one passage is formed in the solid manifold block.

3. The simulator of claim 1, wherein the at least one passages comprises a plurality of fluid tubes formed in a manifold housing of the integral manifold, wherein the plurality of fluid tubes includes a switched pressure tube that provides switched fluid pressure within the manifold housing.

4. An orthopedic simulator comprising:
a frame;
one or more specimen holder assemblies coupled to the frame;
a plurality of actuators coupled to the frame and the plurality of actuators including a movable piston operable to supply a test load or force to one or more test specimens coupled to the one or more specimen holder assemblies; and
an integral manifold that is structurally coupled to the frame and comprising a supply passage within a housing of the manifold and the plurality of actuators being coupled to the supply passage in parallel to provide fluid flow to move the movable pistons of the plurality of actuators to supply the test load or force to the one or more test specimens.

5. An orthopedic simulator comprising:
a frame;
a plurality of test stations including a specimen holder assembly;
an integral manifold comprising a housing coupled to the frame and the housing comprising a fluid passage;
a plurality of actuators coupled to the frame and the plurality of actuators are operable coupled to the fluid passage in parallel; and
a valve assembly disposed between a fluid source and the fluid passage and configured to control fluid flow from the fluid source to the fluid passage to supply fluid flow to the plurality of actuators.

6. The simulator of claim 5 wherein the plurality of actuators include a piston actuator configured to supply a Fx load input to a plurality of test specimens secured to a plurality of specimen holders of the plurality of test stations.

7. The simulator of claim 5 wherein the manifold comprises a first fluid passage and a second fluid passage and the plurality of actuators are coupled to the first and second fluid passages to supply fluid to and discharge fluid from the plurality of actuators.

8. The orthopedic simulator of claim 1 wherein the upper adapter is coupled to the at least one support through a gimbal assembly and the plurality of actuators include at least one actuator configured to apply at least one test load or force through the gimbal assembly and the upper adapter to the test specimen.

9. The orthopedic simulator of claim 1 wherein the plurality of actuators each include a movable piston operable to supply the test load or force and the at least one passage is coupled to a fluid source to supply fluid flow to operate the movable pistons of the plurality of actuators.

10. The orthopedic simulator of claim 1 wherein the frame includes a first support and a second support spaced from the first support and the integral manifold is coupled to the first and second spaced supports to form a cross brace.

11. The orthopedic simulator of claim 10 comprising a plurality of holder assemblies to form a plurality of test stations and the plurality of holder assemblies including the upper and lower adapters and each of the test stations includes one or more actuators configured to supply the test load or force and the one or more actuators of each of the test stations are coupled to the at least one passage of the integral manifold coupled to the spaced supports of the simulator.

12. The orthopedic simulator of claim 11 wherein the plurality of test stations includes at least one actuator coupled to the upper adapters of the plurality of test stations to supply the test load or force through the upper adapters and at least one actuator coupled to the lower adapters of the plurality of test stations and configured to supply the test load or force through the lower adapters and each of the at least one actuator coupled to the upper adapters and the at least one actuator coupled to the lower adapters are coupled to the at least one passage of the integral manifold coupled to a fluid source to supply fluid flow.

13. The orthopedic simulator of claim 12 wherein the at least one actuator coupled to the upper adapters of the plurality of test stations is coupled to each of the upper adapters through a linkage assembly.

14. The orthopedic simulator of claim 1 wherein the plurality of actuators comprise at least one actuator coupled to the upper adapter configured to supply at least one of a Mx, My test load or force and at least one actuator coupled to the lower adapter configured to supply at least one of Mz or Fz test load or force.

15. The orthopedic simulator of claim 4 wherein the plurality of actuators include a first actuator and a second actuator and the second actuator is configured to supply a different load or force in a different direction than the first actuator.

16. The orthopedic simulator of claim 4 wherein the simulator includes a plurality of specimen holder assemblies to form a plurality of test stations and the plurality of actuators include a first actuator configured to supply a first force to a first specimen holder assembly and a second actuator configured to supply a second force to a second specimen holder assembly.

17. The orthopedic simulator of claim 16 wherein the first and second actuators are configured to supply the same force to the first and second specimen holder assemblies.

18. The orthopedic simulator of claim 17 and comprising a third actuator configured to supply a third force different from the same force of the first and second actuators and the first and second actuators are fluidly coupled to a pressure passage connected to the supply passage in parallel with the third actuator.

19. the orthopedic simulator of claim 18 wherein the pressure passage is coupled to the supply passage through a valve assembly operable between multiple positions to control fluid flow to the pressure passage.

20. The orthopedic simulator of claim 5 and including a first fluid passage and a second fluid passage coupleable to first and second actuators through the valve assembly to supply fluid to and discharge fluid from the first and second actuators and the first and second fluid passages are fluidly connecteable to a supply passage in parallel with a third actuator and a discharge passage in parallel with the third actuator.

* * * * *

UNITED STATES PATENT AND TRADEMARK OFFICE
CERTIFICATE OF CORRECTION

| | |
|---|---|
| PATENT NO. | : 7,824,184 B2 |
| APPLICATION NO. | : 11/649961 |
| DATED | : November 2, 2010 |
| INVENTOR(S) | : Bradley D. Schulz et al. |

It is certified that error appears in the above-identified patent and that said Letters Patent is hereby corrected as shown below:

Title Page 2, Column 1

Line 23, delete "0,170,361   A1   11/2002 Vilendrer et al.   ...............73/849" and insert --2002/0170361   A1   11/2002 Vilendrer et al.   .............. 73/849--.

Signed and Sealed this
Sixteenth Day of August, 2011

David J. Kappos
*Director of the United States Patent and Trademark Office*